United States Patent
Djordjevic et al.

(10) Patent No.: US 8,291,744 B2
(45) Date of Patent: Oct. 23, 2012

(54) DIFFERENTIAL ULTRASONIC WAVEGUIDE CURE MONITORING PROBE

(75) Inventors: Borislav B. Djordjevic, Severna Park, MD (US); Lawrence L. Rouch, Baltimore, MD (US)

(73) Assignee: Materials and Sensors Technologies, Inc., Glen Burnie, MD (US)

( * ) Notice: Subject to any disclaimer, the term of this patent is extended or adjusted under 35 U.S.C. 154(b) by 556 days.

(21) Appl. No.: 12/481,141

(22) Filed: Jun. 9, 2009

(65) Prior Publication Data
US 2009/0314088 A1  Dec. 24, 2009

Related U.S. Application Data

(60) Provisional application No. 61/059,982, filed on Jun. 9, 2008.

(51) Int. Cl.
*G01N 29/28* (2006.01)

(52) U.S. Cl. ............... 73/1.86; 73/617; 73/609; 73/644

(58) Field of Classification Search ............. 73/1.82, 73/1.86, 617, 644, 609
See application file for complete search history.

(56) References Cited

U.S. PATENT DOCUMENTS

| | | | |
|---|---|---|---|
| 2,565,725 A * | 8/1951 | Frederick et al. ............... 73/644 |
| 3,301,535 A | 1/1967 | Brown | |
| 3,302,044 A * | 1/1967 | Lynnworth et al. ........... 310/333 |
| 4,127,467 A | 11/1978 | Smith | |
| 4,207,901 A | 6/1980 | Nigam | |
| 4,437,332 A * | 3/1984 | Pittaro ............................. 73/597 |
| 4,455,268 A | 6/1984 | Hinrichs et al. | |
| 4,515,545 A | 5/1985 | Hinrichs et al. | |
| 4,559,810 A | 12/1985 | Hinrichs et al. | |
| 4,574,637 A | 3/1986 | Adler et al. | |
| 4,590,803 A | 5/1986 | Harrold | |
| 4,758,803 A | 7/1988 | Thomas, III | |
| 4,779,452 A | 10/1988 | Cohen-Tenoudji et al. | |

(Continued)

FOREIGN PATENT DOCUMENTS

JP  2003-024943  1/2003

OTHER PUBLICATIONS

Intl. Search Report PCT/US2009/046729, Aug. 19, 2009.

(Continued)

*Primary Examiner* — Peter Macchiarolo
*Assistant Examiner* — Rose M Miller
(74) *Attorney, Agent, or Firm* — Pepper Hamilton LLP

(57) ABSTRACT

The present invention is seen to provide a new methodology, testing system designs and concept to enable in situ real time monitoring of the cure process. Apparatus, system, and method for the non-destructive, in situ monitoring of the time dependent curing of advanced materials using one or more differential ultrasonic waveguide cure monitoring probes. A differential ultrasonic waveguide cure monitoring probe in direct contact with the material to be cured and providing in situ monitoring of the cure process to enable assessment of the degree of cure or cure level in a non-cure related signal variances (e.g., temperature) independent calibrated response manner. A differential ultrasonic waveguide cure monitoring probe including a transducer coupled to a waveguide and incorporating correction and calibration methodology to accurately and reproducibly monitor the cure process and enable assessment of cure level via ultrasonic reflection measurements. The amplitude of the corrected interface response signal reflected from the probe-resin interface indicating changes in the modulus of the material during the cure.

19 Claims, 22 Drawing Sheets

U.S. PATENT DOCUMENTS

| | | | |
|---|---|---|---|
| 4,874,948 A | | 10/1989 | Cielo et al. |
| 4,891,591 A | | 1/1990 | Johnston et al. |
| 4,904,080 A | | 2/1990 | Afromowitz |
| 4,921,415 A | | 5/1990 | Thomas, III et al. |
| 5,009,104 A | | 4/1991 | Johnson |
| 5,159,838 A | * | 11/1992 | Lynnworth ............ 73/644 |
| 5,207,956 A | * | 5/1993 | Kline et al. ............ 264/40.6 |
| 5,439,566 A | | 8/1995 | Zucker |
| 5,777,230 A | * | 7/1998 | Vandervalk ............ 73/632 |
| 5,804,725 A | | 9/1998 | Posakony et al. |
| 5,911,159 A | | 6/1999 | Choo et al. |
| 5,979,233 A | | 11/1999 | Johnson |
| 5,996,415 A | * | 12/1999 | Stanke et al. ............ 73/597 |
| 6,490,501 B1 | | 12/2002 | Saunders |
| 6,644,122 B2 | | 11/2003 | Borowczak et al. |
| 6,675,112 B1 | | 1/2004 | Chadwick |
| 7,114,373 B2 | * | 10/2006 | Hazelden et al. ............ 73/54.02 |
| 7,245,371 B2 | | 7/2007 | Wang et al. |
| 2002/0159557 A1 | | 10/2002 | Jones et al. |
| 2006/0123914 A1 | | 6/2006 | Pena et al. |
| 2007/0282333 A1 | | 12/2007 | Fortson et al. |

OTHER PUBLICATIONS

Djordjevic, B.B. et al., "Cure Monitoring by Ultrasonic Reflection Coefficient", Proc. SAMPE-ACCE-DOE, Sep. 27-28, Detroit, MI., 1999.

Djordjevic, B.B. et al, "In situ Ultrasonic Cure Monitoring Sensors", Proc. 43 Int'l SAMPE 98 Symposium, May 31-Jul. 4, pp. 967-967, Anaheim, CA., 1998.

Djordjevic, B. B., "Ultrasonic Cure Monitoring", CP497, Nondestructive Characterization of Materials IX, R.E. Green, Jr., Ed., 1999, American Institute of Physics, 1-56396-911, pp. 388-392.

Djordjevic, B.B., "Ultrasonic Cure Monitor", ASNT, 17th Annual Research Symposium & Spring Conference, Anaheim, CA., 2008, Paper Summaries, ISBN 978-1-57117-177-1, pp. 58-62.

* cited by examiner

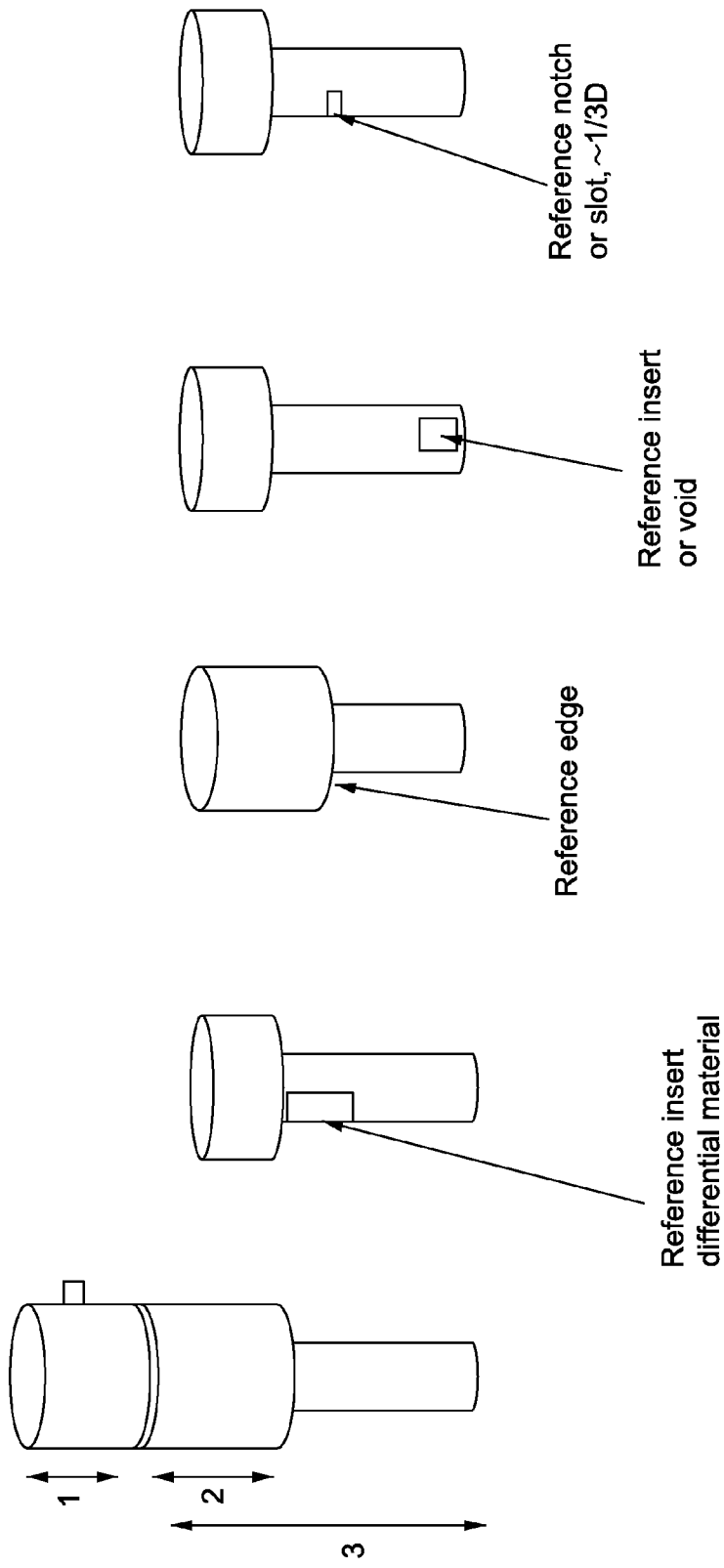

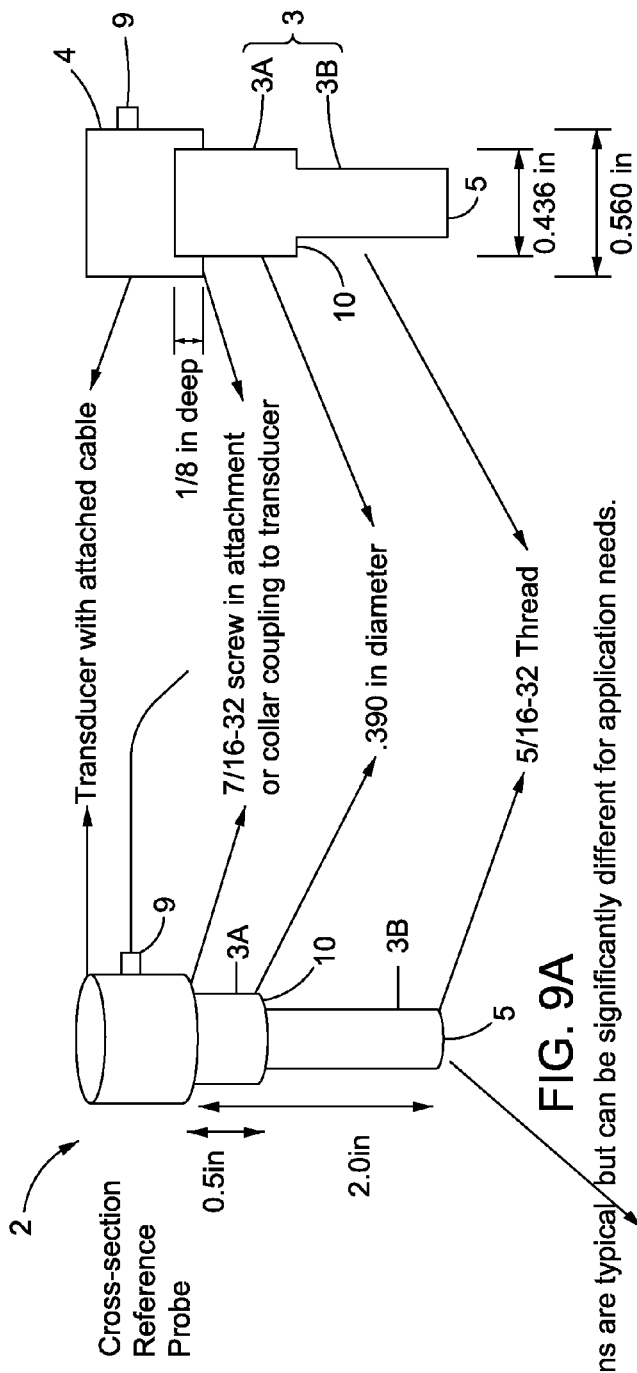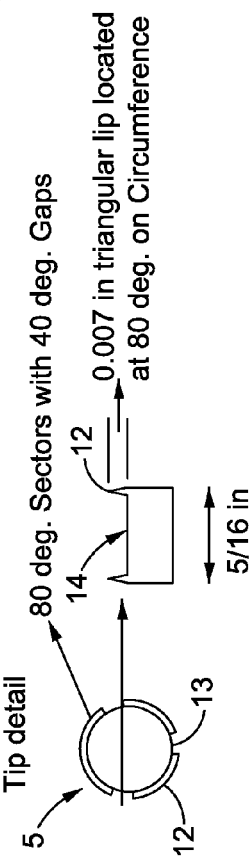

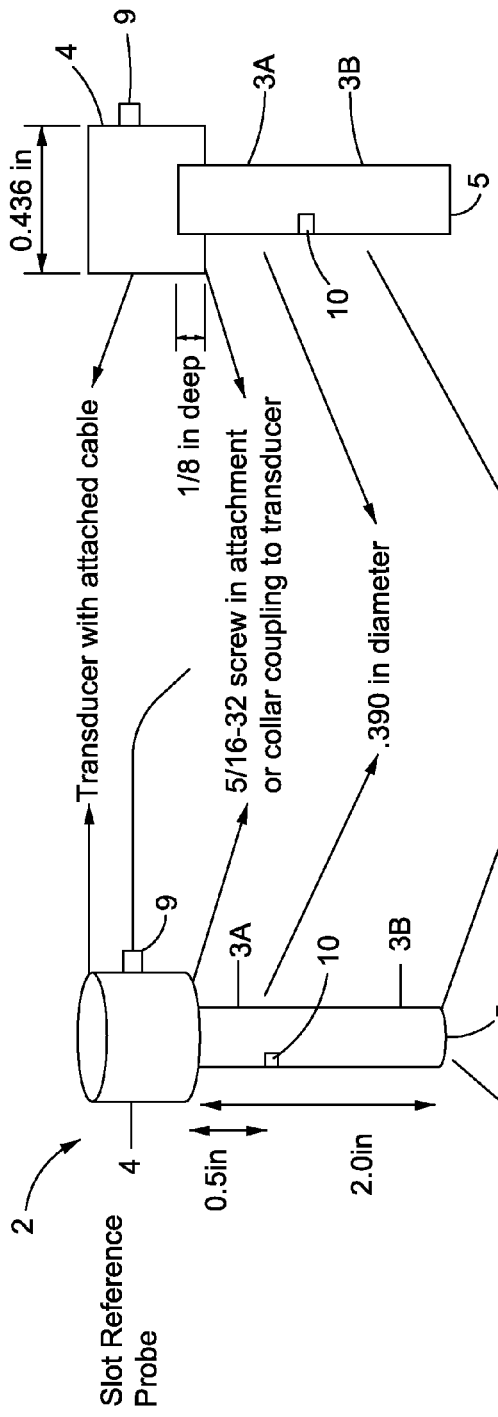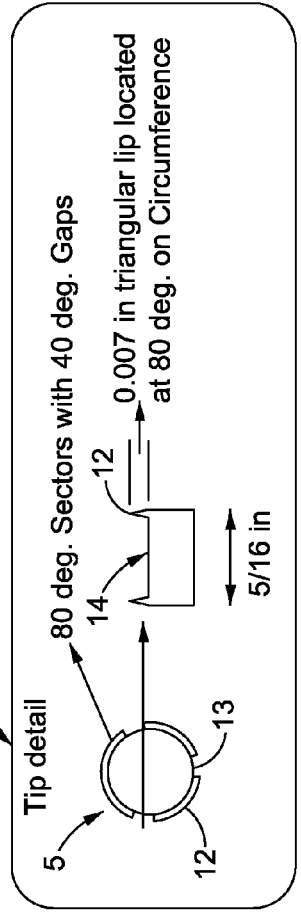
FIG. 10A FIG. 10B FIG. 10C FIG. 10D

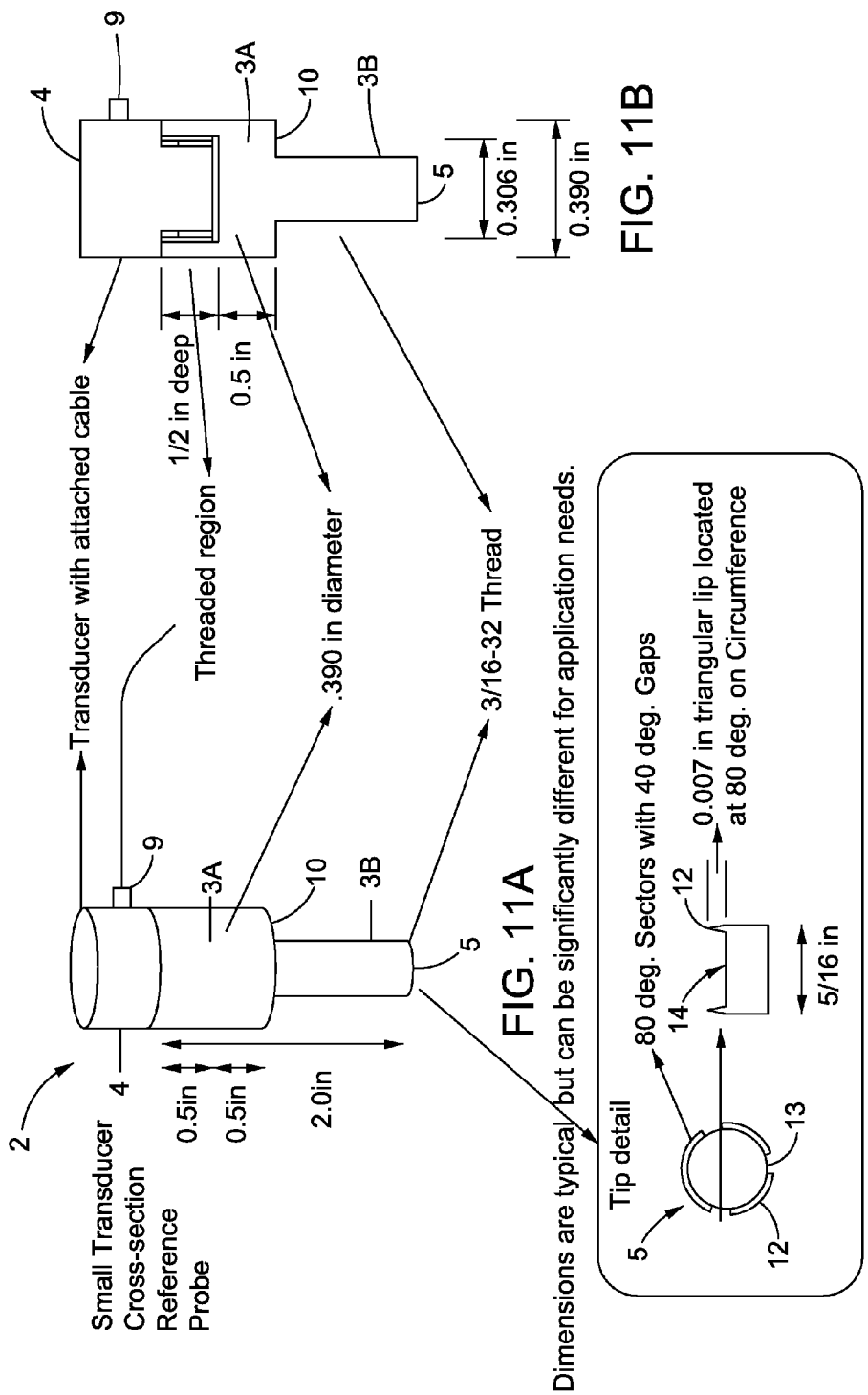

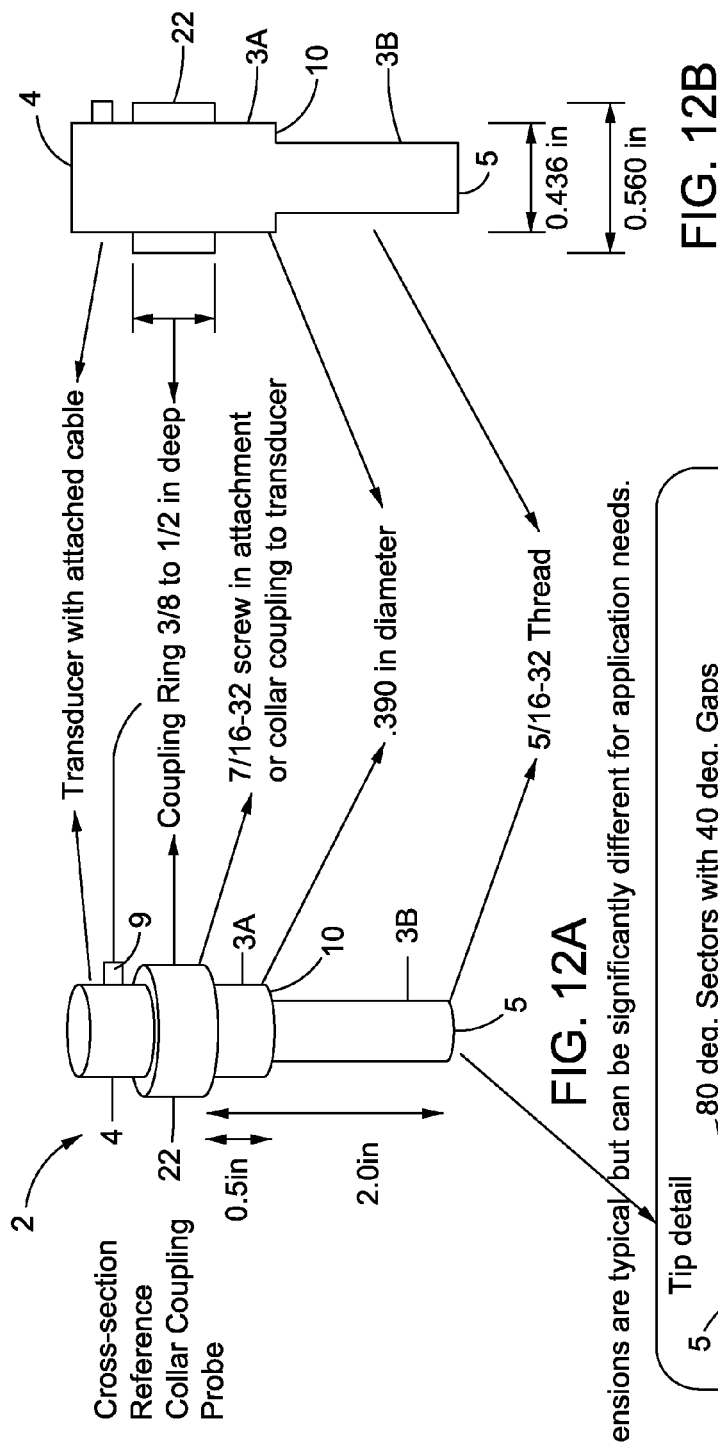
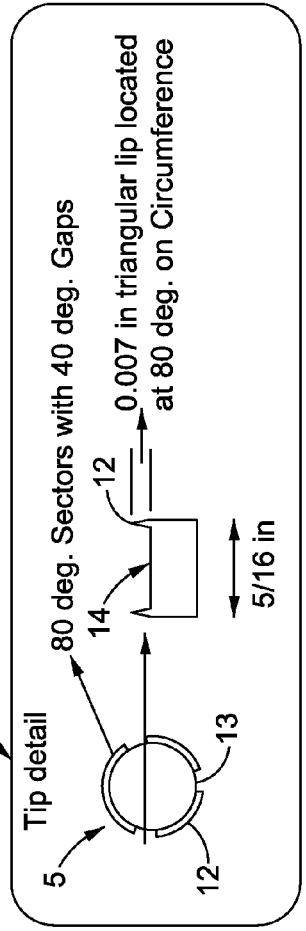
FIG. 12A
FIG. 12B
FIG. 12C
FIG. 12D
Dimensions are typical but can be significantly different for application needs.

Sound path reflection at selected critical angle

Sound path via reflection from the tip angle

Multi-site surface reflection geometry waveguide termination

Composite material

DIFFERENTIAL ULTRASONIC WAVEGUIDE CURE MONITORING PROBE

CROSS REFERENCE TO RELATED APPLICATIONS

This application claims the benefit of U.S. Provisional Patent Application 61/059,982 filed Jun. 9, 2008, the disclosure of which is being incorporated herein by reference in its entirety.

TECHNOLOGY FIELD

The present invention relates generally to the real time, in situ monitoring of materials undergoing a cure process, and more particularly, to a differential ultrasonic waveguide cure monitoring probe for monitoring of the cure process for materials that undergo a cure process to enable assessment of cure level via ultrasonic reflection measurements in a reproducible, environmentally stable, temperature independent calibrated response manner.

BACKGROUND

Cure monitoring and assessment of the cure completion is performed via extensive application of many technologies. Most conventional technologies require testing of witness coupons or samples cut out from the structure. Testing of witness coupons or actual samples of the material being cured is not real time and is an inaccurate means of assessing cure state of the actual structure material. Sampling methodology does not always result in satisfactory assessment of the curing conditions of the structure. For example, localized samples from larger polymer or composite structures often are not representative of the actual cure state of the material resulting in incomplete or unsatisfactory cure information.

In situ cure monitoring, among others, has been performed via various means, including optical, electrical, electromagnetic, mechanical and ultrasonic methods. Ultrasonic methods, for example, provide an advantage of directly sensing the mechanical modulus change of the curing material and thus directly monitor the structural cure of the matrix material. Widely demonstrated in a variety of curing applications, conventional ultrasonic measurements required to monitor and quantify the degree of cure can be cumbersome, expensive and requires complex set up and calibration procedures that make the application of this technology impractical for everyday use. Simple, real time and reproducible in situ cure monitoring is a significant problem facing many manufacturing applications. Current methodologies are inadequate for practical and economic ultrasonic cure monitoring needs for various cure applications, such as aerospace, civil, marine and related industries.

Several patents describe ultrasonic techniques for cure monitoring and some explore ultrasonic reflection for the potential cure monitoring. For example, U.S. Pat. Nos. 5,009,104 and 6,644,122 describe ultrasonic cure monitoring and evaluation of advanced materials and composites. Further, there is a group of ultrasonic cure patents that utilize time of flight (ultrasonic wave transit time) or signal loss (attenuation) measurement approaches (see e.g., U.S. Pat. Nos. 4,455,268; 4,515,545; 4,559,810; 5,911,159; 6,675,112) to monitoring materials modulus and cure state. Furthermore, embedded thin waveguide sensors explore cure effects on the waveguide walls and corresponding change to acoustical signal in and around different configuration waveguides (see e.g., U.S. Pat. Nos. 5,911,159; 4,904,080; 4,574,637; 4,590,803; and U.S. Patent Publication No. 2006/0123914). Some methodologies explore acoustical resonance (e.g., U.S. Pat. No. 4,758,803). Although physically correct, these approaches are entirely impractical and difficult to implement because of extensive and expensive tooling needs for multiple transducer, general loss of transducer after each process and the need to accurately measure transducer separation distances and ultrasonic wave travel times. U.S. Pat. No. 6,644,122 is directed to an ultrasonic cure monitoring process and describes a very general approach to cure monitoring; however this reference does not describe a sensing functionality or measurement process and simply states that the ultrasound responds to cure processes as a measurement tool. A majority of other patents, such as U.S. Pat. Nos. 7,245,371; 4,891,591 and 4,874,948 rely on other indirect sensing technologies that utilize non-mechanical, physically different means of estimating cure. However, none of the noted patents describe or teach a reproducible, differential and calibration approach of cure monitoring as in the embodiments of the present invention. Without the simplification of the test configurations, implementation of differential probes and implementation of calibration methods—the cure level measurements are arbitrary and have very limited engineering and applications value.

The present inventor's initial experiments utilizing ultrasonic cure using direct reflection coefficient (as reported in B. Boro Djordjevic "Cure Monitoring by Ultrasonic Reflection Coefficient", Proc. SAMPE-ACCE-DOE, September. 27-28, Detroit, Mich. 1999 and B. Boro Djordjevic, B Milch "In-situ Ultrasonic Cure Monitoring Sensors" Proc. 43 Int'l SAMPE 98 Symposium, pp 967-967, May 31-July 4, Anaheim Calif. 1998) were successful in identifying an ultrasonic cure process, but impractical because of the unpredictable influence and variances in non-cure related signal variances, such as variances in temperature effects, variances in pressure effects, variances in transducer response, variances in waveguide response, and unspecified variances in instruments calibration effects that did not allow quantitative assessment of cure affected ultrasonic reflection signals and made impossible true comparison of the material cure level.

What is needed is a system and method that uses a direct, differential and calibrated approach for in situ monitoring of materials undergoing a cure process to ensure practical, reproducible, and comparable measurements of the cure process and degree of cure.

SUMMARY

There has been summarized above, rather broadly, the prior art that is related to the present invention in order that the context of the present invention may be better understood and appreciated. In this regard, it is instructive to also consider some of the objects and advantages of the present invention.

It is an object of the present invention to provide an improved monitoring of the cure process via direct ultrasonic means that enable direct, reproducible and calibrated estimate of the materials' degree of cure.

It is another object of the present invention to provide in situ monitoring of the cure during materials' processing operations thus minimizing process errors and subsequent requirements to test state of the cure completion.

It is yet another object of the present invention to enable automate calibration and estimate of the cure material modulus change, cure process materials modulus changes and final material cure state in reproducible and comparative engineering manner.

It is a further object of the present invention to provide a method and apparatus including signal processing requirements and cure probe arrangements that enable ultrasonic reflection based cure monitoring tests in a variety of materials manufacturing operations such as and including, among others: autoclave composite manufacturing, vacuum bagged oven cure and resin transfer molding composite manufacturing.

It is still a further object of the present invention to provide generic methodology to provide means to automatically maintain real time cure process information and enable use of this information by the cure processing apparatus and especially enable real time cure process tracking and cure process optimization to prevent and predict problems and failures.

These and other objects and advantages of the various embodiments of the present invention will become readily apparent as the invention is better understood by reference to the accompanying summary, drawings and the detailed description that follows.

Recognizing the need for the development of improved apparatuses, systems, and methods for materials cure monitoring, the present invention is generally directed to satisfying the needs set forth above and overcoming the disadvantages identified with prior art devices and methods.

In accordance with the present invention, the foregoing need can be satisfied by providing an in situ differential ultrasonic waveguide probe that enables real time monitoring of materials cure state via ultrasonic reflection measurements in a non-cure related signal variances (e.g., temperature) independent calibrated response manner.

According to one embodiment of the invention, a differential ultrasonic waveguide cure monitoring probe is provided for in situ ultrasonic monitoring of a material undergoing a cure process. The differential ultrasonic waveguide cure monitoring probe includes an ultrasonic transducer connected to a waveguide. The waveguide includes a proximal end in contact with the ultrasonic transducer and a distal end for contacting the material undergoing the cure process. The waveguide also includes a first portion extending from the proximal end, a reference, and a second portion extending from the reference to a tip at a distal end of the waveguide. An ultrasonic signal may be generated by the ultrasonic transducer and transmitted into the waveguide. An interface signal may be generated by a portion of the ultrasonic signal reflecting back from the interface of the probe and the material undergoing a cure. The interface signal is reflected back to the ultrasonic transducer and is used to directly sense the mechanical modulus change of the curing material. A reference signal may be generated by a portion of the ultrasonic signal reflecting back from the reference. The reference signal is reflected back to the ultrasonic transducer and may be used to recalibrate the probe and account for non-cure related signal variances during the cure process. A quantitative assessment of a cure level of the material undergoing the cure process may be determined in a non-cure related signal variances independent calibrated response manner using the reference signal to correct/recalibrate the interface signal.

According to one aspect of the invention, the reference of the differential ultrasonic waveguide cure monitoring probe includes one of: a cross-sectional reference; a slot reference; a small transducer cross-section reference; an insert/void reference.

According to another aspect of the invention, the differential ultrasonic waveguide cure monitoring probe comprises an alternate geometry, the alternate geometry including an angled body wherein the second portion of the waveguide extends at an angle relative to the first portion of the waveguide.

According to another aspect of the invention, the differential ultrasonic waveguide cure monitoring probe is in direct contact with the material undergoing the cure process, the probe is only connected to one side of the material being cured, and the cure monitoring is performed in situ to allow real time monitoring of the cure process.

According to another aspect of the invention, the differential ultrasonic waveguide cure monitoring probe is initially calibrated before the cure process begins using a material having known characteristics and wherein the probe is continuously calibrated during the cure process using the reference signal to account for non-cure related signal variances during the cure process in order to provide quantitative assessment and comparison of cure rates and degree of cure completion.

According to another embodiment of the invention, an in situ method for monitoring the cure of a curable material is disclosed. The method includes initially calibrating the differential ultrasonic waveguide cure monitoring probe by reference to the final from a material having a known impedance. The differential ultrasonic waveguide cure monitoring probe may then be coupled to a material to be cured, the differential ultrasonic waveguide cure monitoring probe comprising an ultrasonic transducer and a waveguide extending from the ultrasonic transducer. The differential ultrasonic waveguide cure monitoring probe may be positioned with a tip and front face of the waveguide in direct contact with the material to be cured. The method continues with generating a pulse of ultrasound energy using the ultrasonic transducer and directing the pulse of ultrasound energy through the waveguide toward the material being cured. A portion of the ultrasound energy is reflected back from a reference structure of the waveguide and a portion of the ultrasound energy is reflected back from a materials boundary interface between the probe and the material being cured. The ultrasound energy reflected from the materials boundary interface between the probe and the material being cured may be sensed, as well as the ultrasound energy reflected from the reference. The method provides for correcting the sensed ultrasound energy reflected from the materials boundary interface using the sensed ultrasound energy reflected from the reference. As a result, a real time measurement of the modulus of the material being cured at a particular point in the curing process may be determined using the sensed ultrasound energy reflected from the materials boundary interface and from the reference.

According to another aspect of the invention, the step of sensing the ultrasound energy reflected from the materials boundary interface further comprises: analyzing the amplitude of the reflected ultrasound energy from the materials boundary interface and the reference; periodically analyzing the amplitude of the waveform of the reflected ultrasound energy from the materials boundary interface to determine whether the modulus of the composite has reached a predetermined modulus; and terminating the cure process once the predetermined modulus is reached.

According to another aspect of the invention, the step of correcting the measurement further comprises continuous in situ non-cure related signal variances compensation of the ultrasound energy reflected from the materials boundary interface using the ultrasound energy reflected from the reference to ensure accurate and reproducible sensing of the cure material during the cure process.

According to another aspect of the invention, the step of correcting the measurement further comprises continuous in situ temperature recalibration of the ultrasound energy reflected from the materials boundary interface using the ultrasound energy reflected from the reference to ensure accurate and reproducible sensing of the cure material during the cure process.

According to yet another aspect of the invention, a series of pulses of ultrasound energy, and corresponding reflected reference signals and reflected interface signals, are generated and sensed over a period of time at predetermined time intervals.

According to another embodiment of the invention, a differential ultrasonic waveguide cure monitoring system is provided. The system includes a differential ultrasonic waveguide cure monitoring probe coupled to a computer. The differential ultrasonic waveguide cure monitoring probe includes: an ultrasonic transducer for generating and sensing ultrasonic signals; a waveguide connected to and extending from the ultrasonic transducer; the waveguide for transmitting ultrasonic signals; a reference for reflecting a reference signal back to the ultrasonic transducer; and a front face of the waveguide for contacting a material to be cured and forming an interface between the differential ultrasonic waveguide probe and the material to be cured; the interface reflecting back an interface signal from the interface to the ultrasonic transducer. The computer may include: an input device for receiving information relating to the reference signal and the interface signal; a processor for analyzing the information relating to the reference signal and the interface signal, and for distinguishing the propagation differences between the response signal and the interface signal to estimate the cure material modulus to determine a quantitative cure state of the material in a non-cure related signal variances independent calibrated response manner; a data storage device for storing one or more of: the information relating to the reference signal and the interface signal, information relating to the material being cured, and information relating to the cure process; and an output device for outputting one or more of: the information relating to the reference signal and the interface signal, information relating to the material being cured, and information relating to the cure process.

According to one aspect of the invention, the differential ultrasonic waveguide cure monitoring probe may be integrated into new computerized cure process monitoring system. According to another aspect of the invention, the differential ultrasonic waveguide cure monitoring probe may be retrofit into existing materials processing assemblies. Further, tooling mounting options may be provided for coupling the differential ultrasonic waveguide cure monitoring probe to the material to be cured.

Thus, there has been summarized above, rather broadly, the present invention in order that the detailed description that follows may be better understood and appreciated. There are, of course, additional features of the invention that will be described hereinafter and which will form the subject matter of any eventual claims to this invention. Additional features and advantages of the invention will be made apparent from the following detailed description of illustrative embodiments that proceeds with reference to the accompanying drawings.

BRIEF DESCRIPTION OF THE DRAWINGS

The foregoing summary, as well as the following detailed description of preferred embodiments, is better understood when read in conjunction with the appended drawings. For the purpose of illustrating the invention, there is shown in the drawings exemplary constructions of the invention; however, the invention is not limited to the specific methods and instrumentalities disclosed. Included in the drawings are the following Figures:

FIGS. 8A-8E show different embodiments of an ultrasonic probe including an ultrasonic transducer and a waveguide attachment having a waveguide type reference;

FIGS. 9A-9D show an exemplary cure probe having a cross-section reference;

FIGS. 10A-10D show an exemplary cure probe having a slot reference;

FIGS. 11A-11D show an exemplary cure probe having a small transducer cross-section reference;

FIGS. 12A-12D show an exemplary cure probe having a collar coupling connecting the ultrasonic transducer to the waveguide member;

DETAILED DESCRIPTION OF ILLUSTRATIVE EMBODIMENTS

Figure 1:
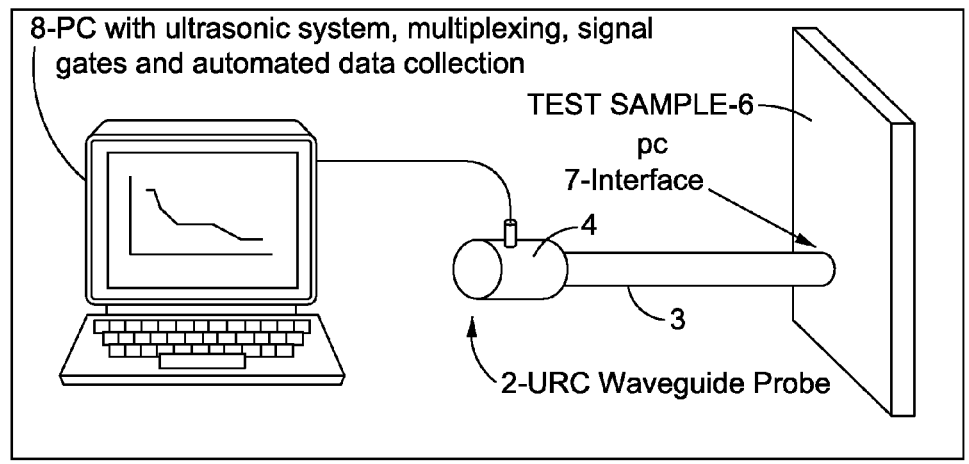
FIG. 1 shows an exemplary system and test bed set up including a differential ultrasonic waveguide cure monitoring probe connected to a materials to cure and a computer system.

Before explaining various embodiments of the present invention in detail, it is to be understood that the invention is not limited in its application to the details of construction and to the arrangements of the components set forth in the following description or illustrated in the drawings. The invention is capable of other embodiments and of being practiced and carried out in various ways. For example, the preferred embodiments disclosed herein are directed to monitoring resins cure; however, it should be understood that these monitoring and detection techniques are applicable to a wide range of structural materials and processes. Also, it is to be understood that the phraseology and terminology employed herein are for the purpose of description and should not be regarded as limiting.

Fabrication of large composite structures with thermosetting polymers requires an understanding of the overall cure cycle, including local cure rates and degree of cure completion. As described supra, there is currently no effective manufacturing method to in situ monitor visco-elastic and mechanic changes in the resin during cure process. During the cure, a thermo-set resin undergoes changes in viscosity, mechanical modulus, density, and ultrasonic velocity. During a cure cycle, the resin material becomes more rigid and starts to behave as a solid. Cured resin has an increased ability to support longitudinal and shear waves with corresponding increased stiffness.

Also described supra, ultrasonic waves have been demonstrated as an effective way to measure the cure process. However, most of the conventional ultrasonic NDE methods are cumbersome, complex and require advanced signal interpretation. The differential ultrasonic waveguide cure monitoring probe of the present invention uses known ultrasonic material (e.g., in the form of a waveguide) coupled into the organic resin and accurately measures changes in signal reflection/transmission due to impedance change in the curing resin. Further, the probe contact interface can be optimized for specific resins to enhance signals and quantitatively track the resin cure cycle.

The following describes the basic physic and measurement concepts associated with the ultrasonic waveguide interface signal reflection measurements. Also described are exemplary processes and modes of operation of improved differential ultrasonic waveguide in situ cure monitoring probe for the reliable and inexpensive manufacturing process control of resin, filled resin, fiber reinforced organic matrix composites, and the like. Many composite structures manufacturing operations have need for rugged and inexpensive Nondestructive Evaluation (NDE) sensors suitable for factory and in-field cure process monitoring. Embodiments of the present invention use a differential ultrasonic waveguide cure monitoring probe that is based upon measurement of an ultrasonic Relative Reflection Coefficient (RRC) derived from normalized and differentially corrected Ultrasonic Reflection Coefficient (URC) measurement at the probe resin interface. The differential ultrasonic waveguide cure monitoring probe measurement process enables calibrated and reproducible cure monitoring.

Although a well known physical phenomena, in practice reproducible measurements of the ultrasonic interface reflections are difficult to measure. The practical quantitative monitoring of the interface signal is required to achieve a reproducible cure monitoring process. The reproducibility of the URC measurements is influenced by several factors or non-cure related signal variances, including the materials, the ultrasonic transducers, temperatures, pressures and instrumentation conditions. To achieve URC waveguide probe reproducible calibration over many possible operating conditions, the probe/sensor must measure the acoustic impedance change across a material boundary interface and corrects/recalibrates this measurement to reference factors built into the sensing probe.

By performing initial signal calibration on the differential ultrasonic waveguide cure monitoring probes and continuous non-cure related signal variances compensations, the differential ultrasonic probe arrangement can reproducibly sense the full cure cycle of the resins. Because the differential ultrasonic waveguide cure monitoring probe responds to changes in resin density and sound velocity, the degree of cure can be quantitatively calibrated to determine the cure-state. The differential ultrasonic waveguide cure monitoring probe, integrated with automated data collection system, enables novel in-process composite cure monitoring.

Embodiments of the present invention relate to probes, systems, and methods associated with technology for the in situ ultrasonic monitoring of the cure process of a material that undergo a cure process (e.g., polymer composites and related materials with matrix material). A differential ultrasonic waveguide cure monitoring probe is conceived to enable assessment of cure level via ultrasonic reflection measurements in a non-cure related signal variances independent calibrated response manner. Probe operation combined with appropriate instrumentation enables practical, reproducible and comparable measurement of the cure process and degree of cure for many cure sensing channels and quantitative comparison of the measurement values from test to test.

An ultrasonic waveguide sensor probe and testing system enables detecting materials cure and enables real time, in situ monitoring of structural material cure modulus change. The system operates by distinguishing the propagation differences between various reflection signals modes of ultrasonic stress waves generated in the waveguide probe and at waveguide structural material interfaces. A means, responsive to sensed acoustic signals, for distinguishing the differences between cure states of materials and temperature and process environment dependent factors and other non-cure related signal variances that aid normalized ways for various waveguides and ultrasonic reflection test modes of ultrasonic stress waves so as to identify a cure state of the material.

A differential ultrasonic waveguide cure monitoring probe in accordance with various embodiments of the present invention may be designed to enable continuous, quantitative, temperature corrected in situ cure monitoring on many locations and with quantifiable cure level estimates from different tests and different probes. Via analysis of the reflection signals, the cure probe can be extended to actual estimate of the cure material modulus.

The following describes several embodiments of the invention and experimental measurements that were performed to demonstrate the utility of the invention. To determine cure process of resin systems, ultrasonic measurements were performed using common polymers as a wave-guide material. Typical probe materials may include acrylic (PMMA), polystyrene, polyamide, or the like. The selection of ultrasonic transducers and/or wave-guide materials is dependent on expected resin cure behavior, temperature requirements and desired sensitivity to the end cure condition. For example, for certain applications metals, ceramics, or glass may be used as the waveguide materials.

System

FIG. 1 is a schematic of an exemplary set-up for a short waveguide ultrasonic reflection coefficient (URC) cure monitoring system showing a differential ultrasonic waveguide cure monitoring probe 2 comprising a waveguide 3 and an ultrasonic transducer 4 (pulsar/receiver), a test sample of a material to be cured 6 in contact with a distal end of the probe, and computer system 8 in communication with the ultrasonic transducer 4. As shown, the computer system includes a PC 8 in communication with the differential ultrasonic waveguide cure monitoring probe 2. The computer system 8 and probe 2 may communicate via hard wire (as shown) and/or wirelessly. The computer system is described in more detail below, and may include a fully automated Ultrasonic Reflection Coefficient (URC) system and associated electronics having multiplexing, signal gates, and supporting complete data collection and output. For example, the exemplary system may track ultrasonic signals from the sensor probe spanning automated signal intensity tracking range at better than 60 dB and continuous gated sampling of the signal over a predetermined period of time (e.g., minutes to many days).

The cure monitoring probe 2 arrangement may be suitable for automated operation for truly in situ mechanical monitoring of the cure process and involves no indirect interpretations of the signals, as is the case with, for example, dielectric probe measurements. The differential ultrasonic waveguide cure monitoring probe 2 is preferably capable of economical multiyear service, may be integrated into computerized cure process monitoring or/and may be retrofitted to existing materials processing assemblies and operations.

Figure 2:
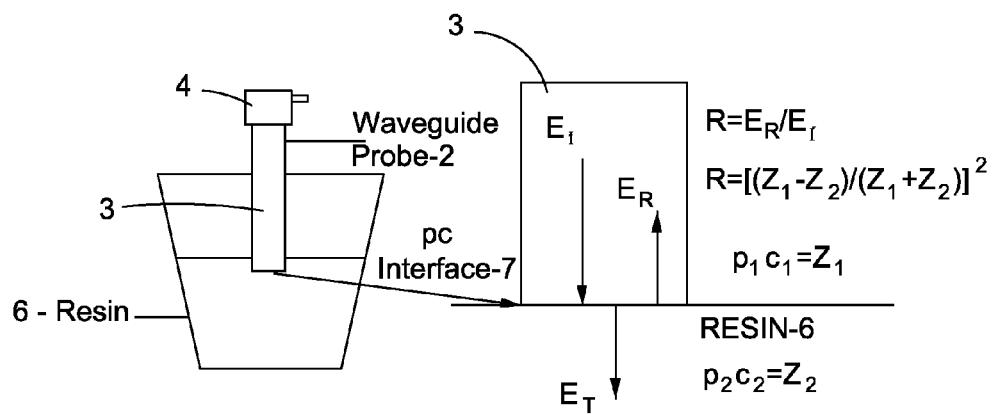
FIG. 2 shows an exemplary measurement set up, for the ultrasonic cure sensor illustrating the sensing interface between a material being cured and a waveguide probe.
Figure 3:
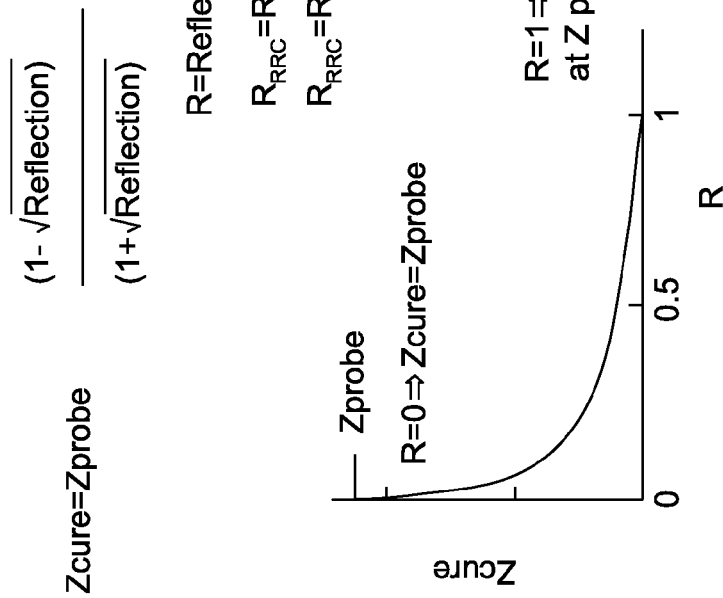
FIG. 3 is a graph showing exemplary critical ultrasonic parameters governing signal interactions at the probe-resin interface defining a relative reflection coefficient ($R_{RRC}$) value.

FIGS. 2 and 3 illustrate typical ultrasonic interface reflection parameters and define differential ultrasonic waveguide cure monitoring probe key test measurement response. FIG. 2 shows an exemplary measurement set-up for the differential ultrasonic waveguide cure monitoring probe 2 based on short wave-guide probe, where R is reflection coefficient, Z is acoustical impedance, $\rho$ is density and c is velocity of sound. $E_I$ represents the incident energy imparted to the waveguide by the ultrasonic transducer, $E_R$ represents the energy reflected by the probe/resin interface, and $E_T$ represents the transmission energy. Reflection coefficient R is defined via ration of $E_R$ and $E_I$ or in terms of the difference of the Probe $Z_1$ and resin $Z_2$ impedances. FIG. 3 illustrates reflections at acoustical impedance limits and shows the critical ultrasonic parameters governing signal interactions at the probe-resin interface defining a relative reflection coefficient ($R_{RRC}$) value. Two factors govern the value of $R_{RRC}$ measurements.

Reflection of the signal at the probe-resin interface 7 is function of impedance difference across the probe to resin interfaces. The value of R can range from 0 to 1. Additionally, overall signal level of the reflection is function of the probe temperature, surrounding pressure and other environmental effects. The reference signals discussed later undergo commensurate changes but are not influenced by resin properties. The probe reference signal relative changes provides additional correction factor to create fully normalized and corrected values for the $R_{RRC}$ measurements. By knowing the impedance of the probe one can calculate the impedance of a resin from the level of the signal reflection. The probe reflections can also be calibrated by reference to the signal from the known impedance liquid. Thus, the differential ultrasonic cure monitoring probe signals can be interpreted quantitatively with respect to the measured cure condition and the final state of the resin cure.

The basic system (e.g., a transducer/waveguide, ultrasonic instrument, electronic instrumentation with means for signal storing and signal processing) can be adapted to different configurations by changing the set-up geometry, changing the transducer, and/or by changing waveguide types. By changing waveguide wave-front (i.e., the tip), frequency and reflection angle directivity, the stress waves ultrasonic tests may be controlled and the apparatus may achieve enhanced performance to detect specific types of cure conditions.

An exemplary application would be a waveguide cure tip set at critical reflection angle at specified resin cure modulus. At the point the resin reaches the specified modulus, reflection signal level at the probe tip would drastically change and essentially create a switching signal. Such response can be used for a simplified cure monitoring process that senses the critical pre-set cure level of the resin.

Probe

Figure 4:
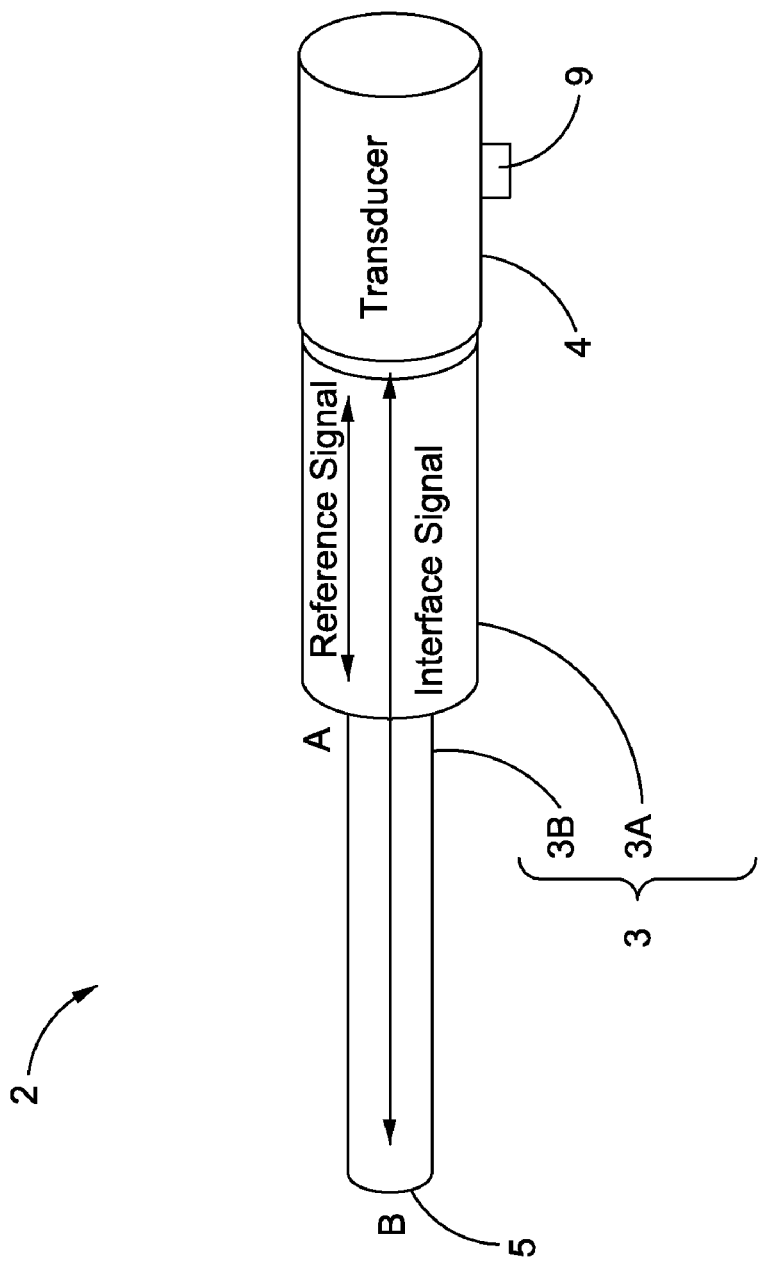
FIG. 4 shows an exemplary and simplified embodiment of the ultrasonic probe, including an ultrasonic transducer and a waveguide sensing extension that provides a sound reflection path for interface signal sensing used for cure monitoring and reference signal sensing used for in situ continuous probe calibration.

Embodiments of the present invention provide in situ differential ultrasonic waveguide probes that enable real time monitoring of materials' cure state. FIG. 4 shows an exemplary differential ultrasonic waveguide cure monitoring probe 2 inclusive of ultrasonic transducer 4 and attached waveguide sensing extension 3 that provides a sound reflection path for the "Interface Sensing," used for cure monitoring, and a "Reference Signal," for in situ continuous probe calibration. Also shown is a connection 9 for connecting the probe 2 to an ultrasonic instrument, a computer system and/or electronics.

As shown, a reference structure 10 may be provided as part of the waveguide 3 (see e.g., location A). A Reference Signal may be generated by a transmitter of the transducer 4, travels through a first portion 3A of the waveguide 3 to the reference 10, and then back to a receiver of the transducer 4. The Reference Signal may be used to compensate for non-cure related signal variances including, for example, transducer/probe changes/effects due to overall operational environmental effects, temperature changes, and/or pressure changes. An Interface Signal may be generated sending a signal from a transmitter of the transducer through a first portion 3A and a second portion 3B of the waveguide 3 to a probe tip 5 in contact with the curing material. The Interface Signal then travels back from location B to a receiver of the transducer.

As such, two ultrasonic signals are measured for the different probes (i.e., a Reference Signal and an Interface Signal). Reference Signal from location A is internal to the probe. The Interface Signal from location B is generated at the probe tip, at the interface between probe and the matrix curing material. The amplitude of the signal reflection at location A and location B may be analyzed to estimate cure level of the matrix. For example, the amplitudes of the reflections at location B corrected by reference signal changes at point A may be analyzed to estimate cure level of the matrix.

In operation, an ultrasonic pulse of selected frequency and pulse shape, originating at transducer 4, may be transmitted via the waveguide 3 to the tip 5 of the probe 2 where a reflected signal is controlled by the impedance properties of the waveguide to curing matrix coupling interface 7. A portion of the initial pulse is reflected as a known Reference Signal from a reference feature 10 built in the sensing waveguide 3. This reference feature 10 may incorporate acoustical reflectors that are part of waveguide such as, for example, a cross-section change, a slot incorporated in waveguide, a different material zone in the waveguide, or any suitable physical feature that will provide a known and stable ultrasonic reflector response.

The interface ultrasonic reflection signal is influenced by probe environmental materials response to temperature and/or pressure. These factors can obscure the true signal response from the interface 7 to the curing material. The Reference Signal is independently influenced by non-cure related signal variances, such as temperature and pressure of the probe environment, and can be used to correct and recalibrate the probe response at the cure sensing interface tip.

This correction/calibration enables non-cure related signal variances (e.g., temperature and/or pressure) independent measurement of the cure state (i.e., matrix modulus estimate) via sensor response that is uniformly calibrated and comparable for different tests with different probes and under different environments. There are many possible waveguide/transducer configurations that enable such measurements. Using linear amplifiers and digital signal capture of the ultrasonic signals, these measurements are readily converted to the physical data that directly tracks cure progress and estimates the matrix modulus change due to cure process.

Signal Response

Figure 5:
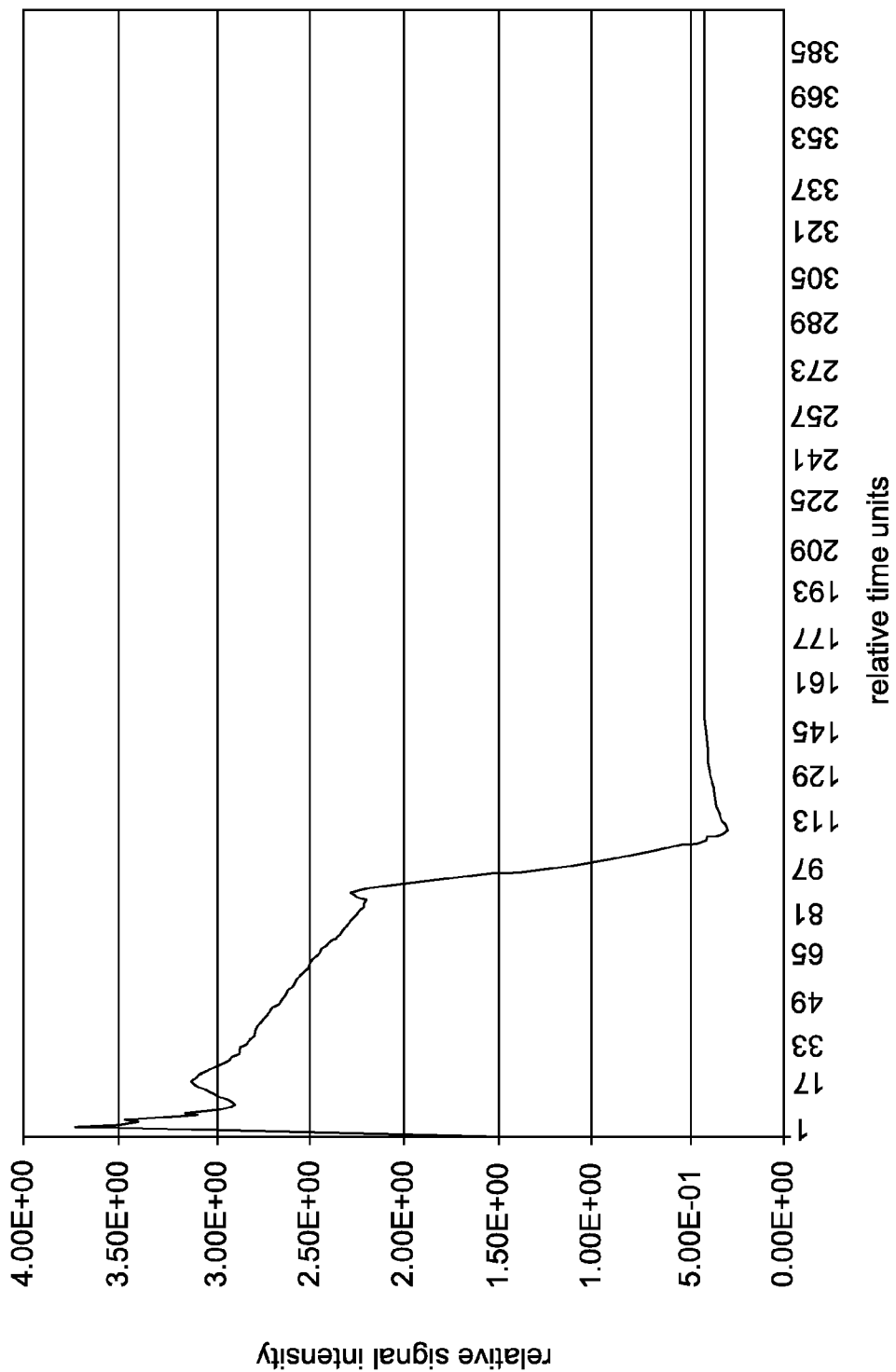
FIG. 5 is a graph showing an exemplary $R_{RRC}$ signal response during cure of polyester resin at room temperature and environment indicating stages of the cure cycle.

FIG. 5 shows an exemplary initial, uncorrected signal response of the resin cure as sensed with the URC monitoring system of FIGS. 1-4 sensing the $R_{RRC}$ signal. As shown in FIG. 5, $R_{RRC}$ signal response during cure of, for example, polyester resin can be measured/monitored at room temperature and environment. Of interest in FIG. 5 is the large dynamic signal range; constant and stable final $R_{RRC}$ signal level; and significant signal changes during different initial cure stages. The graphs show all stages of the thermo-set cure process including gelatin, cure, transition stages, and the final cure level, as sensed by the cure monitoring probe. The horizontal axis represents time and the vertical axis shows the relative signal from the probe.

Figure 6:
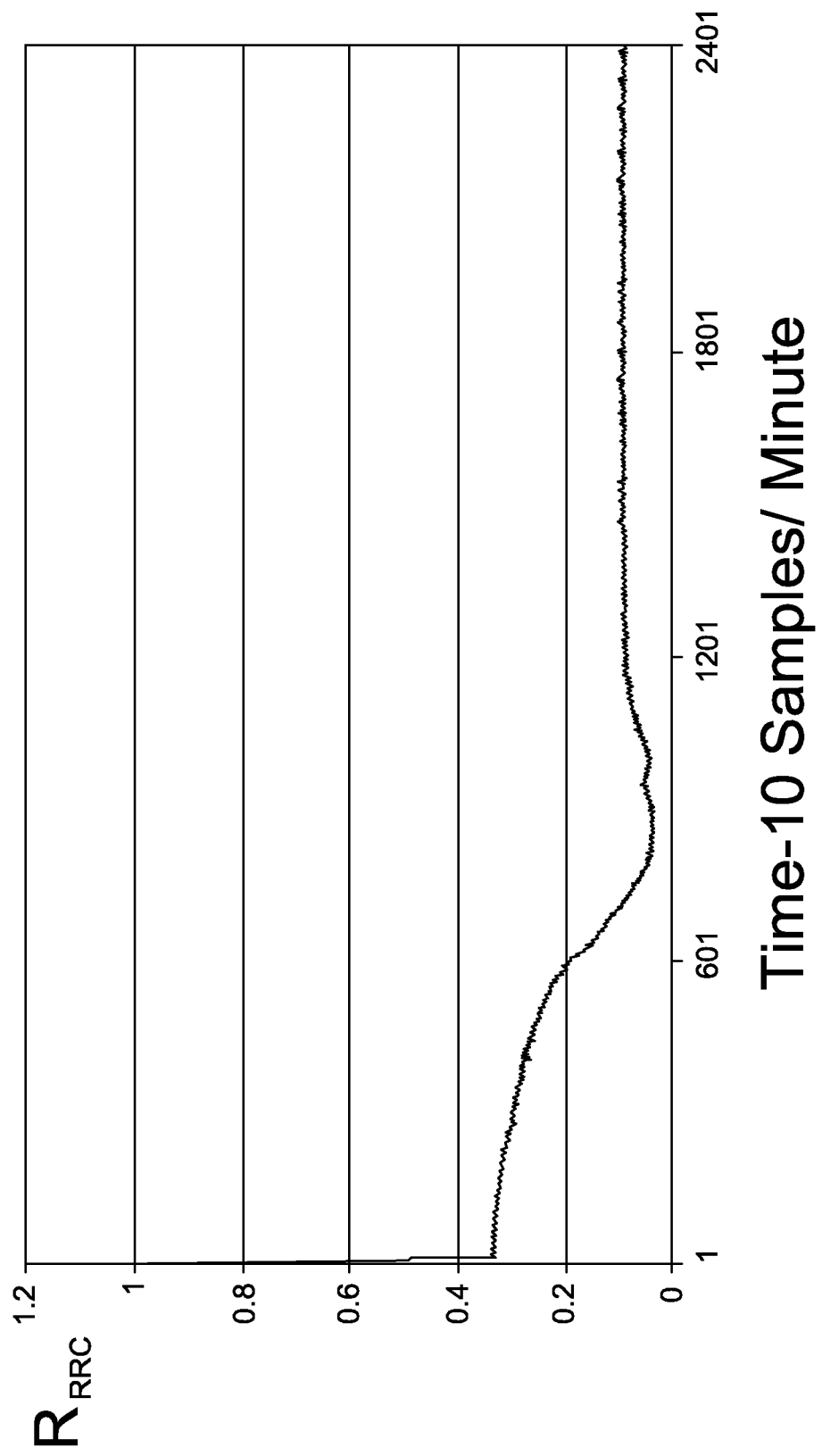
FIG. 6 is a graph showing $R_{RRC}$ versus time for the proper cure of an exemplary fiberglass/polystyrene resin composite during process indicating stages of the cure cycle.
Figure 7:
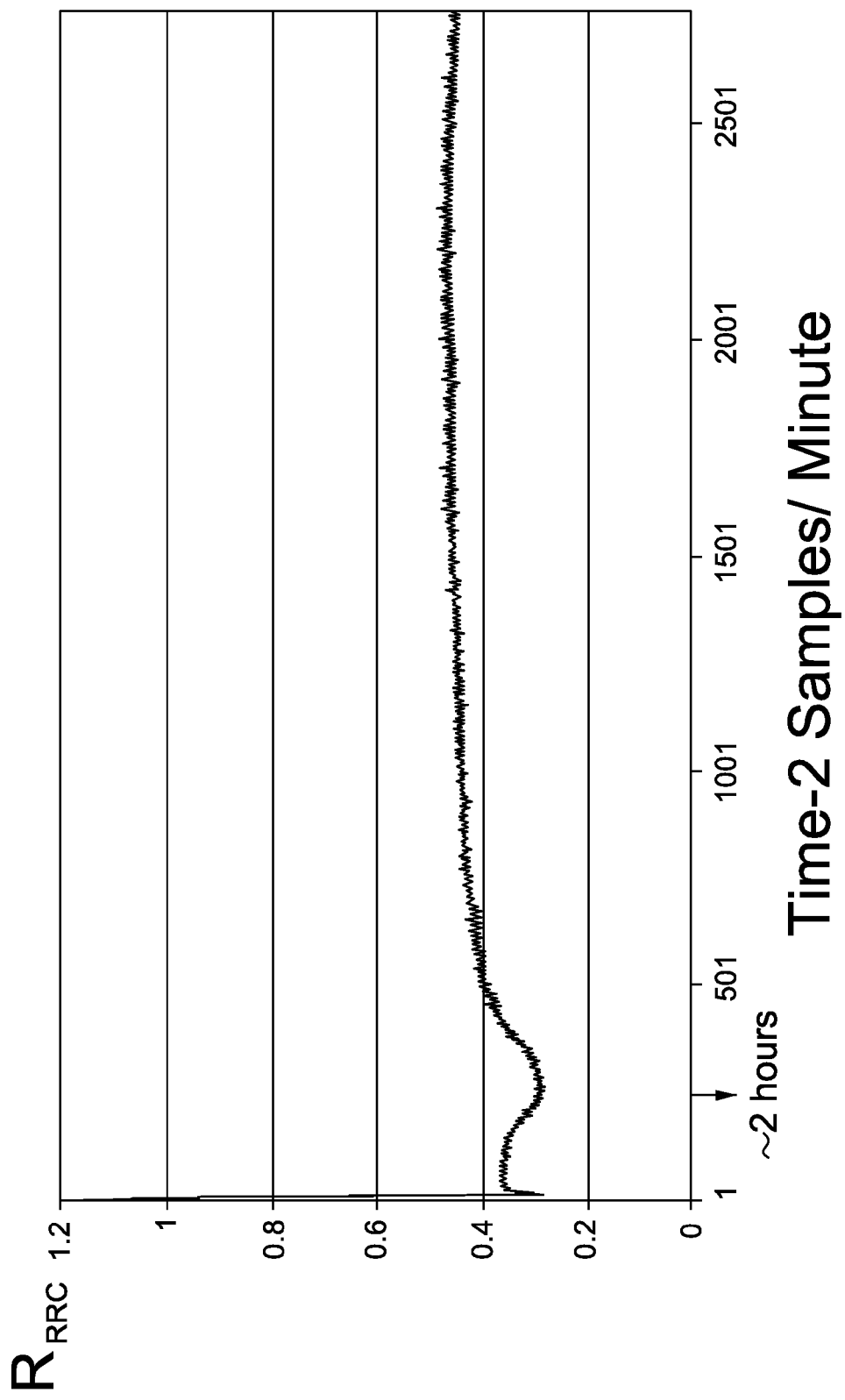
FIG. 7 is a graph showing insufficient cure sensed by response of the $R_{RRC}$ signal from the cure sensor in an exemplary fiberglass/polystyrene resin composite during process indicating insufficient solidification of the material during final stages of the cure cycle.

The signal response signatures shown in FIGS. 6 and 7 are $R_{RRC}$ curves measured during the real time monitoring of the room temperature cure process for an exemplary fiberglass/polyester resin system. Signal response shown is typical data for the process widely used in boat building or construction of large composite decks. The graphs show the thermo-set cure process including transition stages, and the final cure level, as sensed by the cure monitoring probe. The horizontal axis represents time and the vertical axis shows the relative signal from the probe.

One should note the large ultrasonic signal change and the dynamic signal range plotted on the vertical axis that requires good instrumentation and low amplification noise. The polymer cure cross-linking process is consistent with the response of this probe indicating stiffening of the resin with corresponding increase in acoustical impedance of the material. The $R_{RRC}$ index response is controlled by resin mechanical properties and is related to the change in resin density and elastic constants. Such ultrasonic measurements directly sense mechanical condition of the resin and can predict the mechanical condition of the material. The resin cure process generates specific mechanical changes that are identifiable in the sensor response and can be monitored for process verification and control. The sensor only requires one side access and does not depend on distance or time measurements employed by many other conventional ultrasonic cure monitoring methods.

The example of FIG. 6 shows the relative reflection coefficient ($R_{RRC}$) versus time for the proper cure of the fiberglass/polystyrene resin composite during process indicating stages of the cure cycle. As shown in FIG. 6, a $R_{RRC}$ signal shape from a good cure process where the signal reaches a low level threshold and stabilizes at constant value indicating completion of the cure process.

FIG. 7 illustrates insufficient cure as sensed by response of the $R_{RRC}$ signal from the cure sensor in a fiberglass/polystyrene resin composite during a cure process indicating insufficient solidification of the material being cured. As shown in the example of FIG. 7, a $R_{RRC}$ signal from an inadequate cure process where resin never reaches desired cure state and the cure process after more than 41 hours has not stabilized. The incomplete cure process could be due to possible improper resin formulation, over-aged resin components, low environment temperature or externally contaminated resin. Regardless of the improper cure origin, the $R_{RRC}$ value indicates lack of resin mechanical and chemical consolidation and positively records insufficient material processing conditions.

A basic differential ultrasonic waveguide cure monitoring probe test configuration, such as shown in FIGS. 1-3 and with probe configuration as shown in FIG. 4, enables direct and reproducible measurements of the mechanical cure state of the resin material. Because impedance of the resin is a product of the density and sound velocity of the resin material, the interface B reflection is a function of the resin impedance change due to cure process. As the resin cures, the resin ultrasonic velocity changes proportionally to the resin mechanical modulus change. As a result, the reflection coefficient at interface B is affected and represents the modulus change of the curing resin. Temperature, pressure and environmental factors (collectively non-cure related signal variances) can modify reflection values at interface location B of the waveguide probe and resin system. These same factors or non-cure related signal variances affect signals at the interface location A that is built in as a reference reflection signal in the waveguide probe. The signal reflections at location A that are independent of the resin are used to correct, and normalize response signals from location B, thus creating stable and reproducible reflection coefficient measurements of the resin at location B, and minimizing effects of environmental factors. Such differential arrangement with initial system normalization calibration enables the reflection measurements at location B to be directly correlated to the actual mechanical modulus of the resin.

A single probe with supporting ultrasonic data acquisition system can be used at any desired location in the composite curing arrangement to monitor a local cure process by continuous recording of the reflection signal from interface locations B and A. In some embodiments, the frequency of the test may generally be between 1 and 10 MHz, and these parameters may be adjusted for the specific cure material and waveguide requirements. For example, larger structures with thicker parts will in general use lower frequencies and proportionally larger probes. For general applications, ultrasonic transducers with 5, 10 and/or 15 MHz test frequencies using nominally ¼ inch to ⅛ inch diameter waveguide, are practical and flexible to sense cure of most thermo-set materials.

Other Probe Configurations

FIGS. 8A-8E show several exemplary probe/sensor embodiments with temperature reference standards for improved differential ultrasonic cure monitoring. As shown in FIGS. 8A-8E respectively, the probe may include: a cross-section reference probe; an insert reference probe; an edge reference probe; an insert/void reference probe; a notch reference probe; and the like. Each embodiment of the differential waveguide cure monitoring probe includes a transducer operatively coupled to a waveguide attachment and a reference incorporated into or formed as part of the waveguide. The shape of the waveguide may vary depending on the application. For example, the waveguide probe may be round or faceted as per application function.

FIGS. 9A-9D show different views and further details of an exemplary cross-section reference differential probe 2 for the hard mount in the tooling surfaces. FIG. 9A shows a perspective view of the cross-section reference probe having an ultrasonic transducer 4 connected to a waveguide body 3. FIG. 9B shows a cross-sectional view of the probe of FIG. 9A and one suitable manner of connecting the ultrasonic transducer 4 and the waveguide body 3. FIG. 9C shows a tip 5 detail and FIG. 9D shows an exemplary surface treatment and triangular lip 12 located on the circumference of the probe tip 5. As shown, the lip 12 may be located intermittingly (e.g., 80 degree sectors) around the tip circumference with gaps 13 (e.g., 40 degrees) in between the lip sectors. The tip may include a surface treatment 14. Surface treatments may include cleaning, etching and possible coating of the probe tip to enhance coupling and adhesion of the probe to the resin material. Surface treatments may vary for different probe materials and may be as simple as solvent wipe and controlled microroughness of the tip surface, for example.

As shown, the waveguide 3 has a first portion 3A having a first cross-section and a second portion 3B having a second cross-section. In the illustrated embodiment, the first portion 3A has a larger cross-section than the second portion 3B. The first portion 3A may be used to measure the reference signal, and the first and second portions 3A, 3B may be used for interface sensing. The probe 2 may include direct mount threads (e.g., 5/16-32 thread) for threaded engagement with corresponding tooling side hole/threads. A probe seal may be provided and may be customized for the specific application, using for example; O-rings, paste, via Teflon tape or similar sealing techniques. This type of probe may be mounted to a modified delay line transducer housings directly or via a coupling ring.

FIGS. 10A-10E show different views and further details of an exemplary slot reference differential probe 2 for the hard mount in the tooling surfaces. FIG. 10A shows a perspective view of the slot reference probe 2 having an ultrasonic transducer 4 connected to a waveguide body 3 with a slot reference 10. FIG. 10B shows a cross-sectional view of the probe of FIG. 10A and a threaded connection between the ultrasonic transducer 4 and the waveguide body 3. FIG. 10C shows a tip 5 detail, and FIG. 10D shows an exemplary surface treatment and triangular lip 12 located on the circumference of the probe tip 5.

As shown, the waveguide 3 has a first portion 3A from the connection between the ultrasonic transducer 4 and waveguide body 3 and extending to the slot 10 and a second portion 3B extending from the slot 10 to the probe tip 5. The first portion 3A may be used to measure the reference signal and the first and second portions 3A, 3B in combination may be used for interface sensing. The probe 2 may include direct mount threads (e.g., 5/16-32 thread) for engaging corresponding threads in a hole in the tooling side. A probe seal may be provided and may be customized for the specific application, using for example: O-rings, paste, via Teflon tape or similar sealing techniques. This type of probe may be mounted to a modified delay line transducer housing directly or via a coupling ring adapter.

FIGS. 11A-11D show different views and further details of an exemplary small transducer cross-section reference differential probe 2 for the hard mount in the tooling surfaces. FIG. 11A shows a perspective view of the miniature screw on cure monitoring probe 2 having a cross-section reference 10. FIG. 11B shows a cross-sectional view of the probe 2 of FIG. 11A and a threaded region wherein the ultrasonic transducer 4 may screw into a hole having corresponding threads in the proximal end of the waveguide body 3. FIG. 11C shows a tip 5 detail at the distal end of the waveguide 3, and FIG. 11D shows an exemplary surface treatment and triangular lip 12 located on the circumference of the probe tip 5.

FIGS. 12A-12D show different views and further details of an exemplary cross-section reference differential probe 2 having a collar coupling 22. As shown, a coupling ring 22 may be used to connect the transducer 4 and the waveguide 3.

Figure 13:
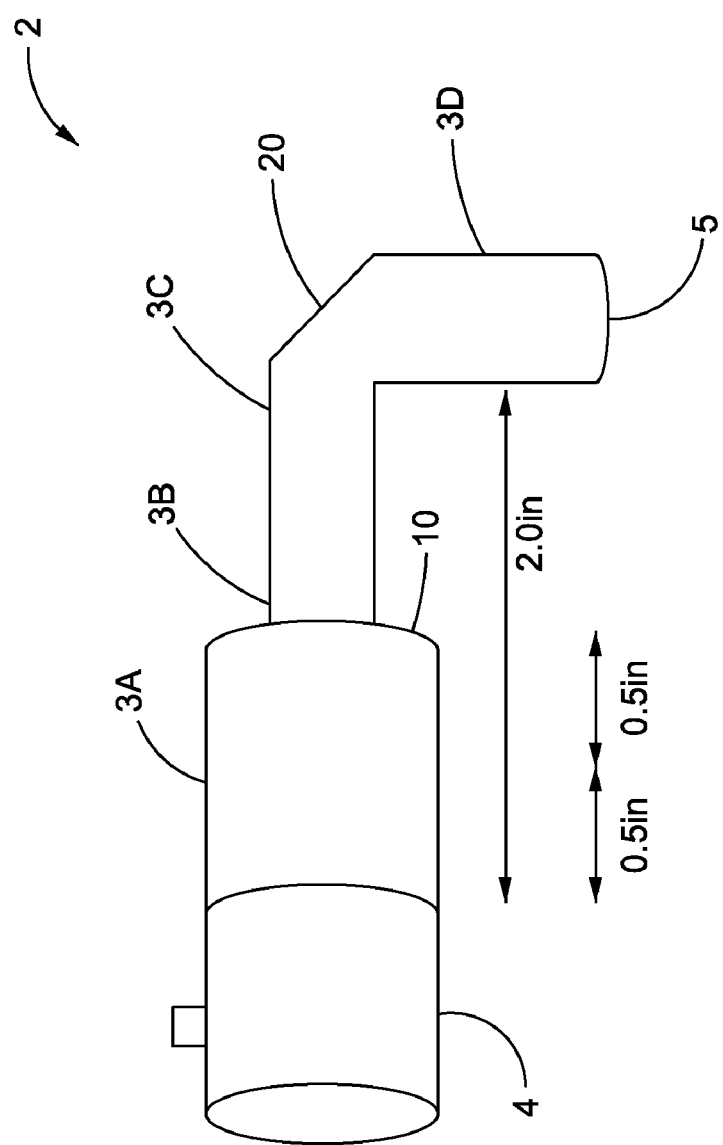
FIG. 13 shows an exemplary cure probe having an alternative waveguide geometry.

FIG. 13 shows an alternate embodiment of the probe 2 having a shaped (e.g., non-linear) waveguide design. For example, the waveguide may include a curved body having a radius or an angled body having corners appropriate to guiding ultrasonic waves to a location per application function. As shown, the waveguide includes a first portion 3A and a second portion 3B. The second portion 3B includes a third portion 3C, a fourth portion 3D, and a corner 20 for redirecting the signal between the third portion 3C and fourth portion 3D. In special designs, the waveguide can be made integral to the composite parts-tooling or the waveguide probe can integrate tooling material or tooling surfaces as an extension to the ultrasonic path of the waveguide.

The probe sensing interface tip 5 can be geometrically modified for the optimum test coupling such as shown for the composite pre-preg cure monitoring where the tip 5 incorporates fiber stand off ridges or lips 12. Additionally, probe waveguide material may be selected for best response to cure changes in the matrix and probe sensing interface may be modified to optimize coupling to the matrix material and the probe. Interface modifications can include surface treatment 14 such as, for example, solvent etch of the surfaces or separate coating of the interface surfaces for optimum vetting and coupling to the resin matrix.

The dimensions shown in FIGS. 9A-13 are exemplary and may vary for different application needs. For example, the probe lengths may be about one inch to in excess of 12 inch.

Figure 14A:
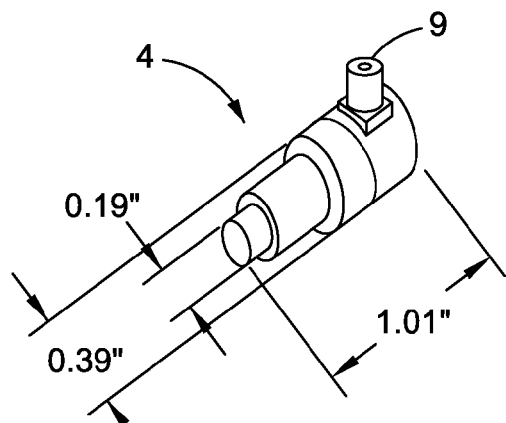
FIGS. 14A-14C show exemplary ultrasonic transducers.
Figure 14B:
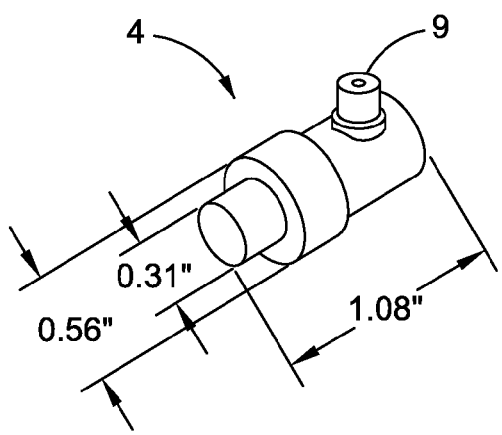
Figure 14C:
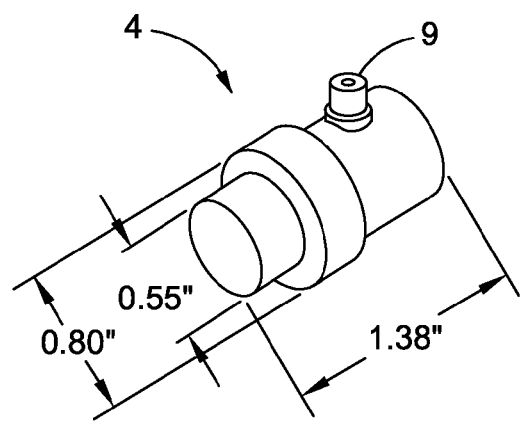

The probes can be designed around standard delay line transducer housings as shown in FIGS. 14A-14C. As shown in the various figures, a probe and transducer may be connected/coupled together using a variety of techniques, such as screwing the two pieces together.

Multi-Probe and Automation

Figure 15:
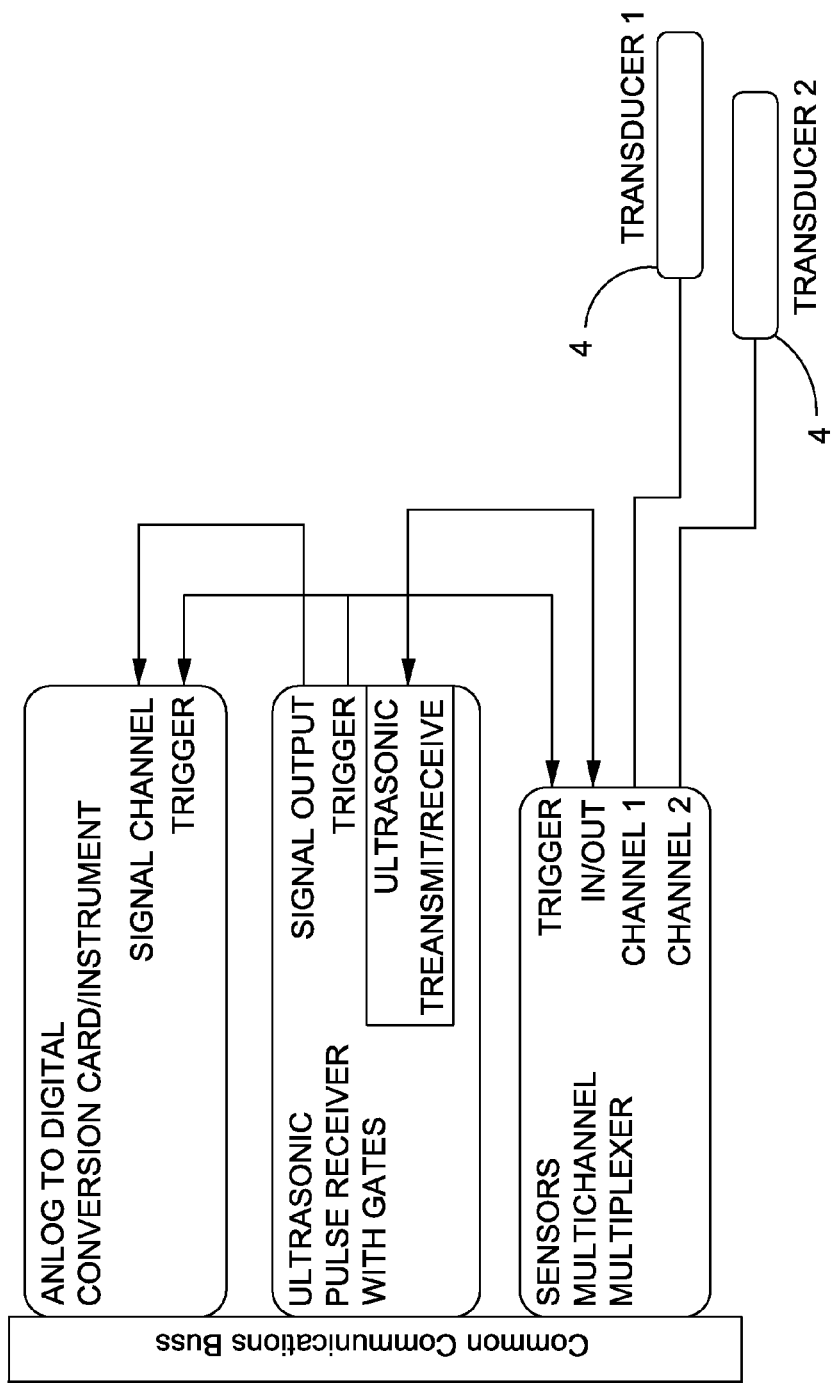
FIG. 15 is a block diagram showing exemplary system hardware, including an A/D board, a pulser/receiver card, and a channel multiplexer board.

FIG. 15 shows a multi-probe set-up and some of the system hardware and electronics. As shown in FIG. 15, the system hardware may including an A/D board 30, an ultrasonic pulser/receiver card, and a channel multiplexer board. One or more differential ultrasonic waveguide cure monitoring probes (e.g., transducer 1 and transducer 2) may be coupled to the system hardware and electronics via wire or wireless means. The MUX board may be used to switch between two different transducers. By analog amplification, gating, digital signal capture, signal processing and digital data analysis and processing, such cure testing/monitoring can be performed totally automated.

The system work as follows:
1) Get calibration signals on transducers.

As shown in FIG. 15, two transducers may be put on the system, one for each channel. On each channel, two numbers may be gathered: the peak amplitude of the signal when the transducer is in air, and the peak amplitude of the signal in a second medium. These numbers should be stored in the file when the data files are created (see step 5 below). For a two probe embodiment, there will be two sets of these peak amplitudes gathered—one for each channel.

2) Set the transducers in the resin to be cured (hardened). Preferably, no software interaction is needed.

3) Set gates.

Gates should be positioned over the signal to be checked. Preferably, there will be at least one gate on the signal. Note that there may be two settings for this gate: one when switched to channel 1, and one when switched to channel 2.

4) Set the recording rate and time to record.

Set how often and how long to collect data. In the illustrated embodiment, data may be collected on channel 1 and channel 2, so the system may switch from channel 1 to channel 2 using the multiplexing function. Preferably, at a low end about 40 to about 100 tests a second are tried, and at a high end a test every minute or so. There should also be a time limit on how long to record data (e.g., 3 minutes, 3 hours, 3 days, etc.)

An ultrasonic transducer, or even remote laser acoustical source, may be used to generate controlled frequency and wave-front ultrasound signal in a waveguide including bulk, shear, and/or other guided mode acoustic waves. Alternatively, a laser light may be delivered to a waveguide surface through mirrors, fiber optic bundles, light pipes or combinations of optical components. FIG. 4 illustrates schematically the arrangement of the elements of an exemplary embodiment of a differential ultrasonic waveguide cure monitoring probe for forming and controlling ultrasonic tests.

The same ultrasonic transducers, or another ultrasonic transducer, or possibly a remote non-contact receiver on the waveguide termination may be used for sensing to help in redirecting the reflected sound fields from the reference and waveguide/resin interface location. Waveguides enable capture of the signal at different angles from multiple locations and allow the receiving transducers to be laced at more flexible locations. Arrays of waveguides enable capture of ultrasonic signals from different sources.

5) Start recording.

A button or remote signal should start recording data. At every collection, the peak amplitudes should be gathered and stored in a file. The option to pause the collection and resume it later may be provided. Data will not be written to the file while the system is paused. Also, there should be a graph of the amplitude data displayed over time (e.g., either linearly or on a log scale).

6) Stop recording.

Recording will stop after the time limit is reached or when it is cancelled by the user.

Data may be collected with a data capture and storage unit, whereupon the data may be processed and decisions may be made with regard to the degree of cure or materials modulus change. Embodiments of the present invention enable one to generate and detect ultrasonic signals from a single location using one waveguide probe coupled ultrasonic transducer. The methodology enables one to control the wave front, frequency, and reflection parameters of the acoustic signal for optimum interaction with the material and detection of the cure process affected ultrasonic interface echoes.

Measurements Concept

The following paragraphs expand the measurements concept of the present invention by providing a specific description of an exemplary measurement process that enables calibrate and quantitative sensing of the cure level in the polymeric materials and composites (i.e., the material to be cured). As described, embodiments of the differential cure monitoring approach extends the measurements of the cure to differential non-cure related signal variances (e.g., temperature) compensating waveguide arrangements. The differential temperature measurements enable practical reproducibility of signals measurements and calibration of the absolute value of the cure levels. Calibration of cure level/degree enables quantitative assessment of the mechanical condition of the polymer resin/composite material, and thus, a significant improvement over current state of the art methodologies that cannot directly and in situ determine actual cure state of the material.

The ultrasonic signals are typical examples of RF or rectified UT echoes that will be gated by a cure signal capture processor. There are several steps to achieve and measure the calibrated reference reflection signal ($R_{RRC}$).

First, the amplitude of the main end point waveguide reflection is measured in air or from a controlled impedance liquid at a determined temperature. For example, room temperature around 25 degrees C. The normalized $R_{RRC}$ reflection is defined and calibrated as 1 by dividing the controlled impedance reflection amplitude measurement by itself for all the channels and transducers.

Thus, regardless of the set-up to set-up and test to test variability of the transducers, waveguides, amplifiers, cables and/or electronics, the cure monitoring sensor initial signal levels are synchronized (e.g., at a value of 1) and comparable to each other. This process assumes linearity of the electronic-transducer system and similar sensing response over the reflection interfaces during the cure processing tests. System linearity is a reasonable assumption with modern electronics customized for these types of measurements.

The $R_{RRC}$ reflection coefficient retains the reference normalization by dividing the reference echo numeric measurement of signal amplitude with the new values of the resin-probe interface signal amplitude—that is by continuous correcting resin-probe interface signal amplitude (Point B) by the changes in the probe internal reference signal measurements (point A), as illustrated in FIG. 4. This procedure assumes linear ultrasonic dynamic range and minimum dispersion effects due to some fundamental frequency variances between the probes. This correction procedure also accounts for and minimizes the variance in individual pulse signal amplitudes due to electronic channel, transducer-probe response, cable and other amplitude affecting differences/variants.

If there were no temperature effects, this calibration itself allows more reproducible measurements of the ρc changes at the probe-resin interface. However, most of the resins exhibit some exothermic heating, temperature is not constant during long cure process, or the cure process is performed in ovens and autoclaves that operate at elevated temperatures and pressure.

Thus, the relative reflection coefficient signal $R_{RRC}$ has to be further corrected by differential reference echo signal that compensates for the temperature effect on the probe (as well as other non-cure related signal variances). One simple way is to utilize and monitor additional echo in each probe that is only affected by temperature and is independent of the resin signal.

This temperature reference signal measurement can be achieved by probe design incorporation signal interface reflectors (i.e., a reference as part of the waveguide) that are dominantly influenced by temperature (or pressure or environmental) effects. As shown in FIGS. 8A-13, for example, there may be a wide range of the possible probe configurations that enable this additional correction.

Overall, the simplest calibration algorithm for $R_{RRC}$ is:

$$R_{RRC} = E_R/E_{Air} X1/(E_{RTemp}/E_{RRef\,Temp})$$

where:

$R_{RRC}$=Relative Reflection Coefficient
$E_R$=Reflected Amplitude at probe resin interface
$E_{Air}$=Reflected Amplitude probe "air" interface
$E_{RTemp}$=Reflected Amplitude from temperature interface
$E_{RRef\,Temp}$=Reflected Amplitude from temperature interface at selected calibration temperature (usually same as $E_{Air}$ measurements)

The measurements of the amplitude can be performed by peak signal detection of the RF ultrasonic signal or peak detection of the rectified and filtered ultrasonic RF signal. In advanced applications with noise problem, the detection can include signal processing such as frequency analysis of the ultrasonic echoes and amplitude (energy) measurement at the selected frequency domain.

Ultrasonic $R_{RRC}$ values may be collected as a function of time and other process parameter, such as temperature. As such, it is possible to develop typical cure process reference curves from, for example, lab controlled resin cure response tests and the development test measurements on actual part configurations. Ultrasonic $R_{RRC}$ response curves may be presented as a function of time and/or process manufacturing steps. These RRC response curves are characteristic of the process and may serve as control and acceptance for the anticipate a cure response.

FIGS. 16-20 show anticipated signal waveforms capture for an exemplary 2.25 MHz transducer signal using standard impulse driven ultrasonic test instrument.

Figure 16:
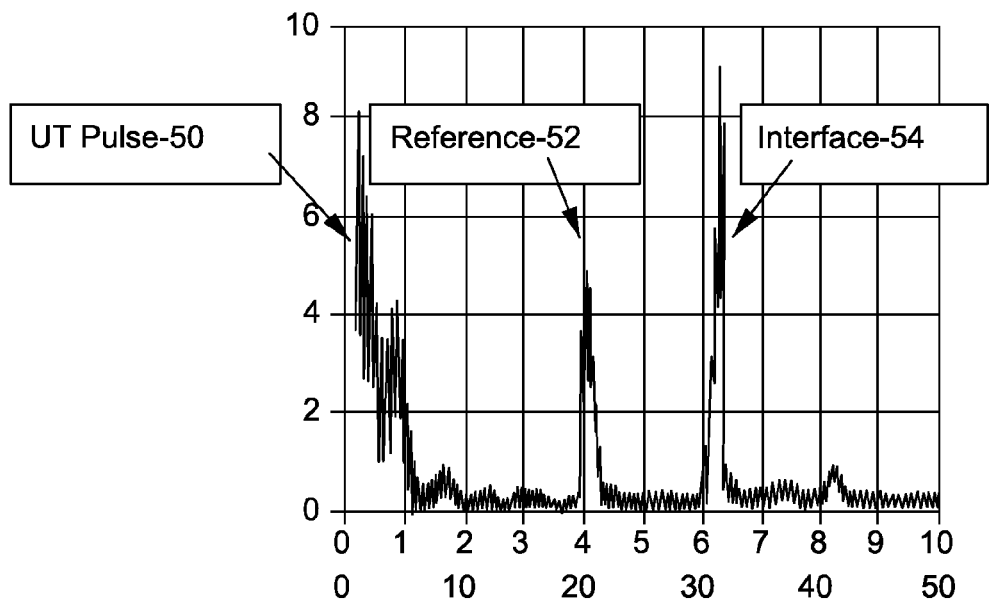
FIG. 16 is a graph showing an exemplary rectified ultrasonic signal showing initial pulse, reference echo, and cure interface echo for an exemplary probe having a slot reference.

FIG. 16 shows an exemplary gated ultrasonic signal showing initial pulse, temperature reference echo and cure interface echo. Signals are for the PMAA 1⅜ inch probe with a reference slot at ⅞ inch (see e.g., FIGS. 10A-10D).

Figure 17:
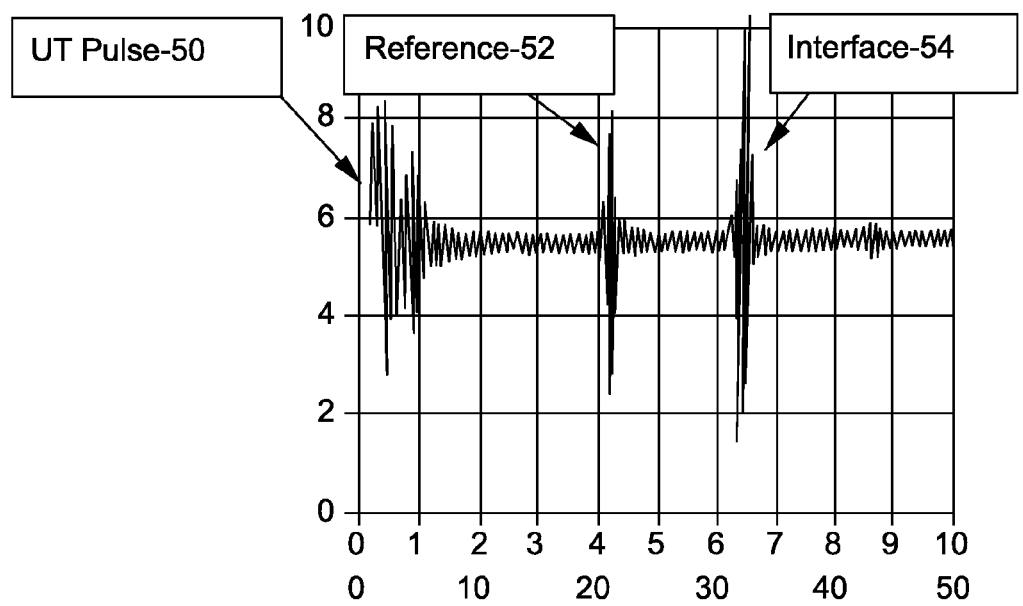
FIG. 17 is a graph showing exemplary RF signals for reference echo and cure sensing interface echo for an exemplary probe having a cut or slot reference.

Exemplary reference and interface RF signals for the 2.25 MHz guided wave probe with a reference slot reflector is shown in FIG. 17. The reference signal is from an exemplary 1/3 cut/slot in the 2 inch long waveguide probe. As shown in FIGS. 16-17, the signal gating options may include, Full rectified and filtered signal as in FIG. 16. Peak detection.

Unprocessed RF signal peak amplitude detection, as in FIG. 17.

+RF signal peak detection.

−RF signal peak detection.

Figure 18:
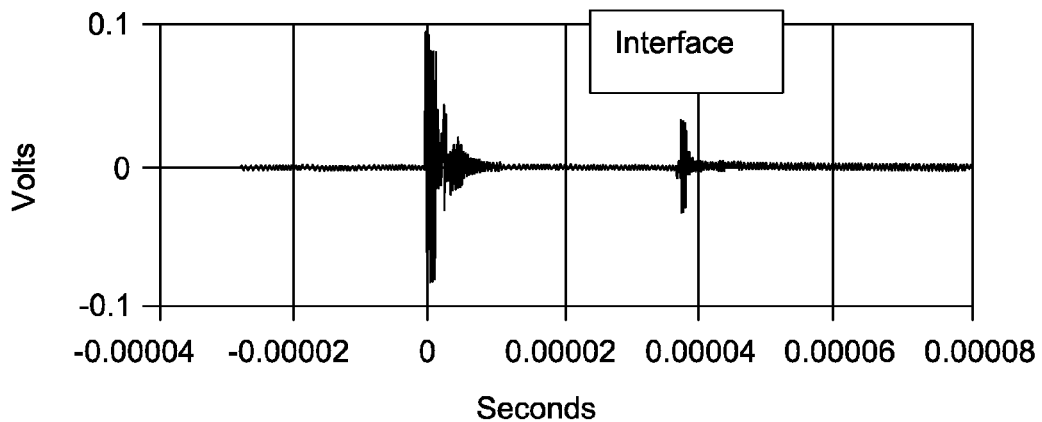
FIG. 18 is a graph showing a generic waveguide ultrasonic waveform signal for an exemplary 2 inch long PMMA probe with drive and reflected air signal from the probe test interface.

FIG. 18 shows a digitally captured and plotted waveguide ultrasonic RF signal in an exemplary 2 inch PMAA probe (¼ inch diameter) with drive and sensing interface reflected air calibration signal.

Figure 19:
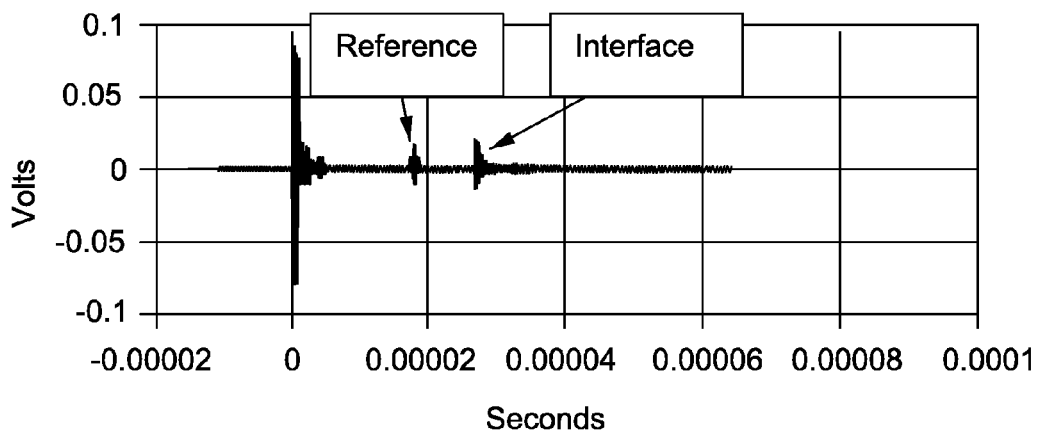
FIG. 19 is a graph showing an exemplary ultrasonic record of a 2.25 MHz signal for an exemplary 1.389 inch long PMMA probe with a slot reference.

FIG. 19 shows an exemplary ultrasonic record of the 2.25 MHz signal with slot reference for an exemplary 1.389 inch PMMA having a reference cut at about 0.494 inch. For nominally 100 V transducer drive pulse at 0.5 μs half-width, a typical voltage of the signal return for a cured resin is expected in the 50 mV to 5 μV. Thus a receiver should be able to resolve around 80 dB signal range or have auto-gain control.

Figure 20:
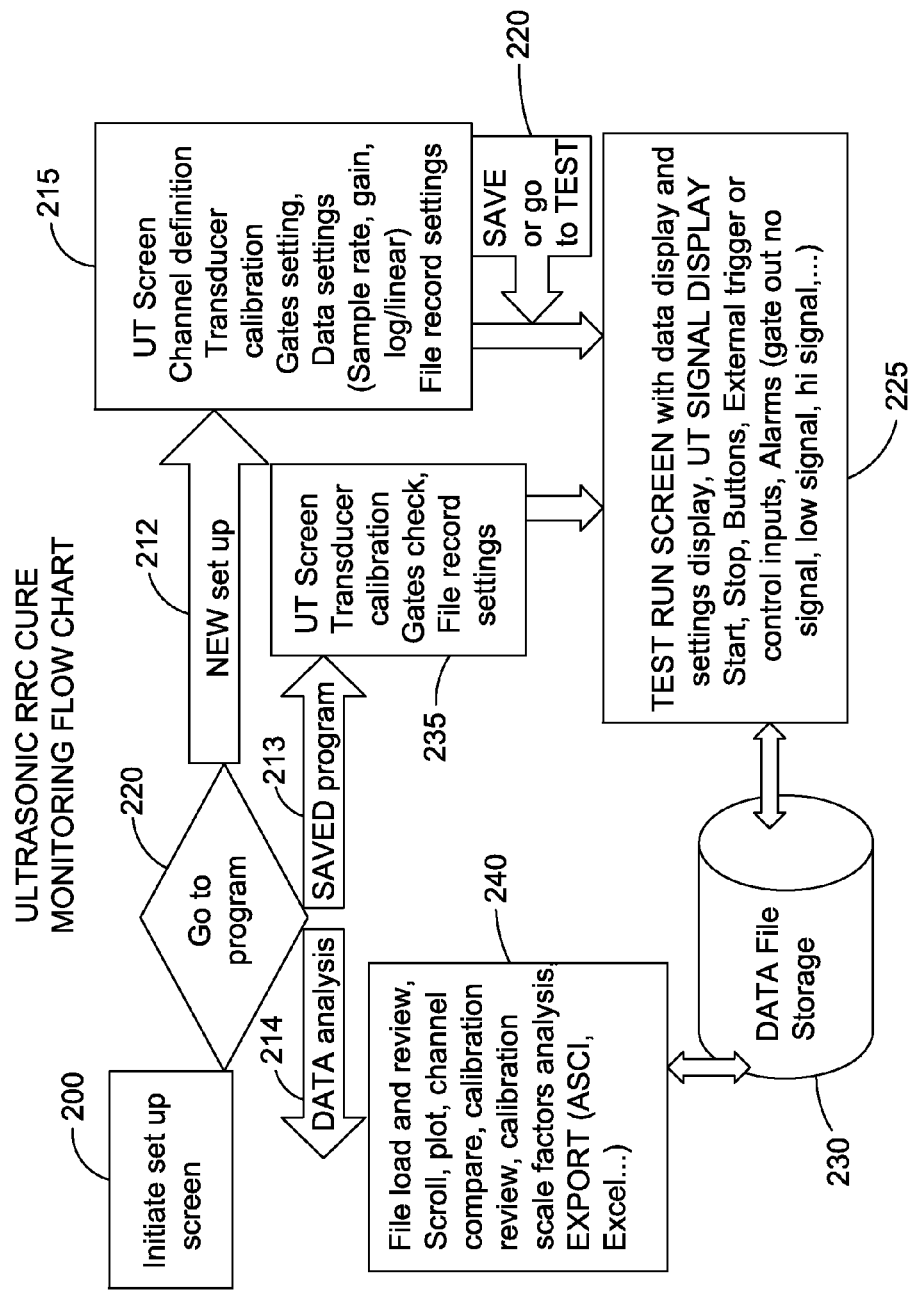
FIG. 20 is a flow chart illustrating an exemplary relative reflection coefficient (RRC) cure monitoring process.
Figure 22:
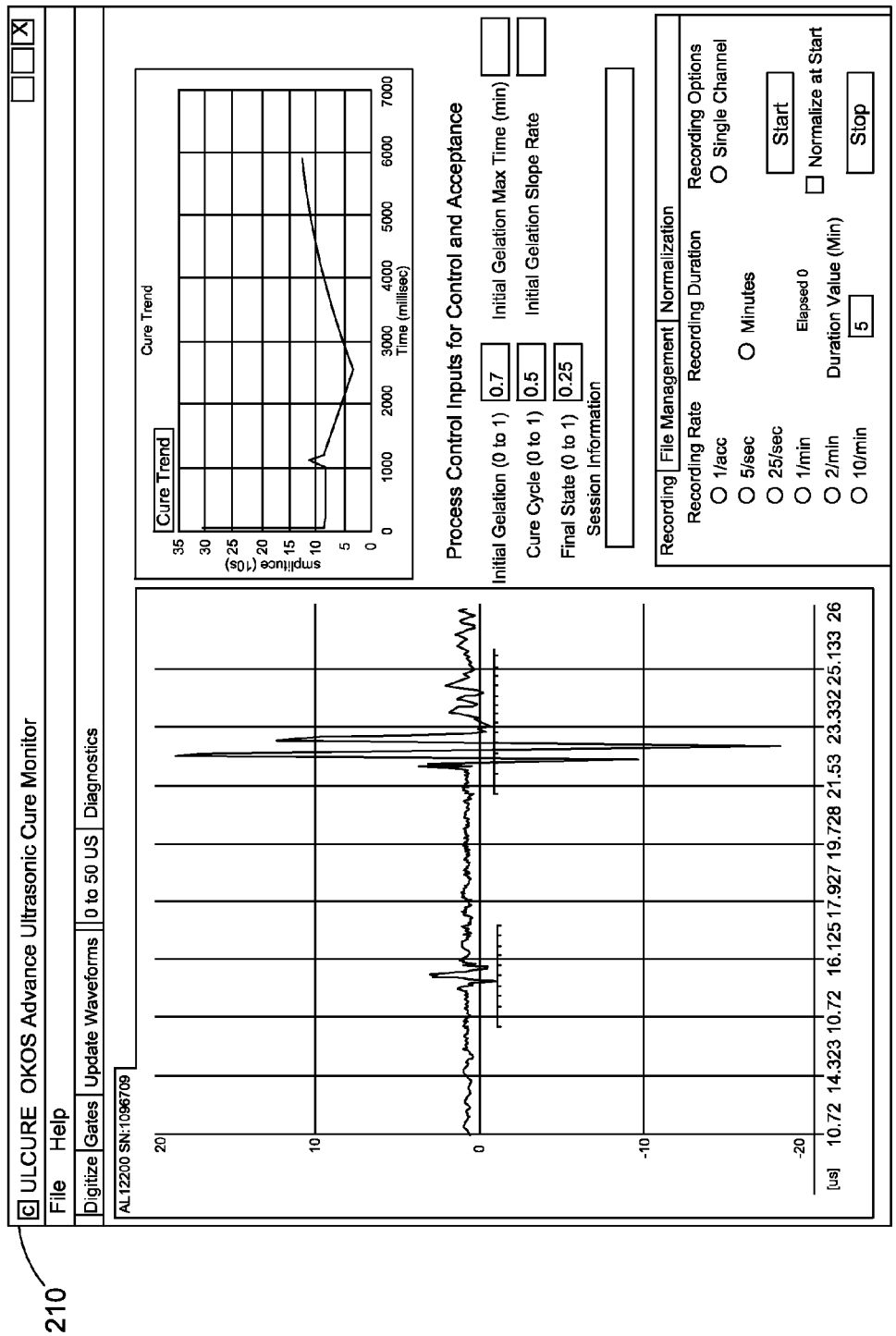
FIG. 22 is an exemplary screen shot of the display of the PC of FIG. 21.

FIG. 20 is a flowchart showing an exemplary process for differential ultrasonic waveguide cure monitoring. As shown in FIG. 20, the process may begin with the user initiating the computer system and electronics Step 200. A display 210 showing an exemplary initial set-up screen is illustrated in FIG. 22. At step 220, the user selects a program to run. The programs may include, for example, a new set-up (step 212), a saved program (step 213), and a data analysis (step 214).

As shown in FIG. 20, at step 215 a new set-up program (212) may display a UT screen that allows the user to perform/select one or more functions including, for example, channel definition, transducer calibration, gates setting, data settings (e.g., sample data rate, gain, log/linear, etc.), file record settings, and the like. Once the new set-up is complete, the user may save it or go to test (step 220). At step 225, the cure monitoring process may proceed with a test run screen with data display and settings display, a UT signal display, start and stop buttons, external trigger or control inputs, alarms (e.g., gate out, no signal, low signal, high signal, etc.). At step 230, the process continues and data file storage may occur.

If a saved program (213) is selected at step 220, the process continues to step 235 and a saved program may display a UT screen, transducer calibration, gates check, file record setting, and the like. The process may then proceed to step 225 and step 230 (described above). If a data analysis program (214) is selected at step 220, the process continues to step 240 and one or more of the following functions may be performed: file load and review, scroll, plot, channel compare, calibration review, calibration scale factors analysis, Export (ANSI, Excel, etc.). The process may also access the data file storage at step 230.

Figure 21:
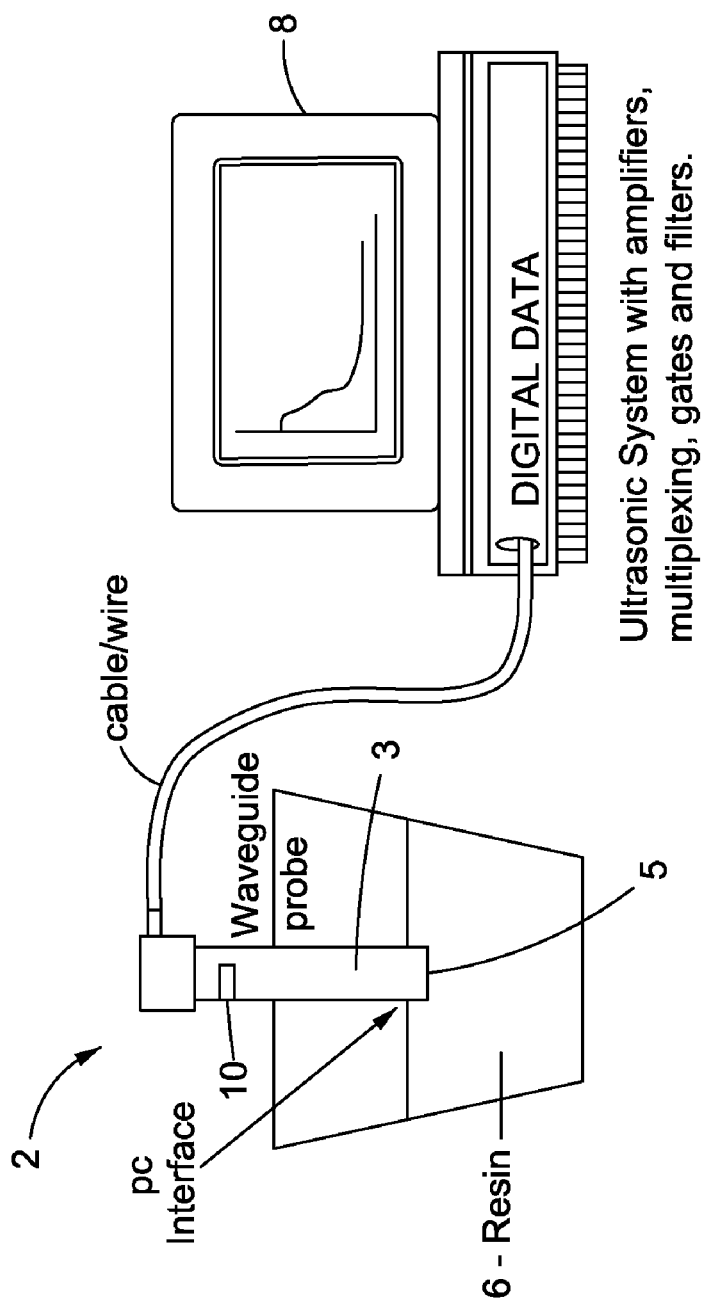
FIG. 21 is an exemplary system showing the cure probe coupled to a PC having multiplexing, signal processing, and automated data collection and processing.

FIG. 21 shows an exemplary test set-up including a differential ultrasonic waveguide cure monitoring probe in contact with a resin material to be cured and connected to a computer having a processing and digital data storage capacity. Display 210 may be part of the computer 8 and may display information regarding the cure process and level of cure to the user. For example, as shown in FIG. 22 the display 210 may include information relating to set channel switch rate, zooming, panning, channel n graph/scope (gate n) display, channel n selection, start, exit, data normalization, gate control, signal marking/tracking, data recording, graph/scope control, file control, and the like.

As noted from FIGS. 20-22, for example, convenience features such as set up recording, graphic presentations or memory access to previous data, may be included in computer monitoring applications. As in all modern computer system, data interchange and interface to other devices, such as process controllers and/or alarms notices, may be provided for integrated manufacturing controls.

Further, a single channel ultrasonic instrument can be extended via electronic and computer multiplexing to any number (n) of channels. This may enable cure monitoring in larger composite processing operations. Depending on the manufacturing needs, individual probes can be located on strategic component locations to locally assess cure process at, for example, the different zones of the parts. This multi-site monitoring may be desirable for products with possible part thickness variance, resin infusion delays, local thermal conditions or a host of other processing needs. In multi-channel operation, each probe data maybe individually recorded, and the probes information may be processed in identical manner as a single probe test procedure.

In multi probe configurations, test data from probes may be compared to established baseline cure data. By comparison of different probes responses, it is possible to make informed engineering decisions on the cure process. The data capture and processing aspect of the present invention may include signal analog amplification, signal gating, and signal capture by digital means with multi-channel capability at resolutions as needed to process the signals. Ultrasonic signals may be gated and analyzed in the time and frequency domains, classified via analysis or other feature and classification algorithms. Dedicated processors and software may be used to automatically characterize or assist in characterization of signal changes that track the differential ultrasonic waveguide cure monitoring probe response.

Computer

Figure 23:
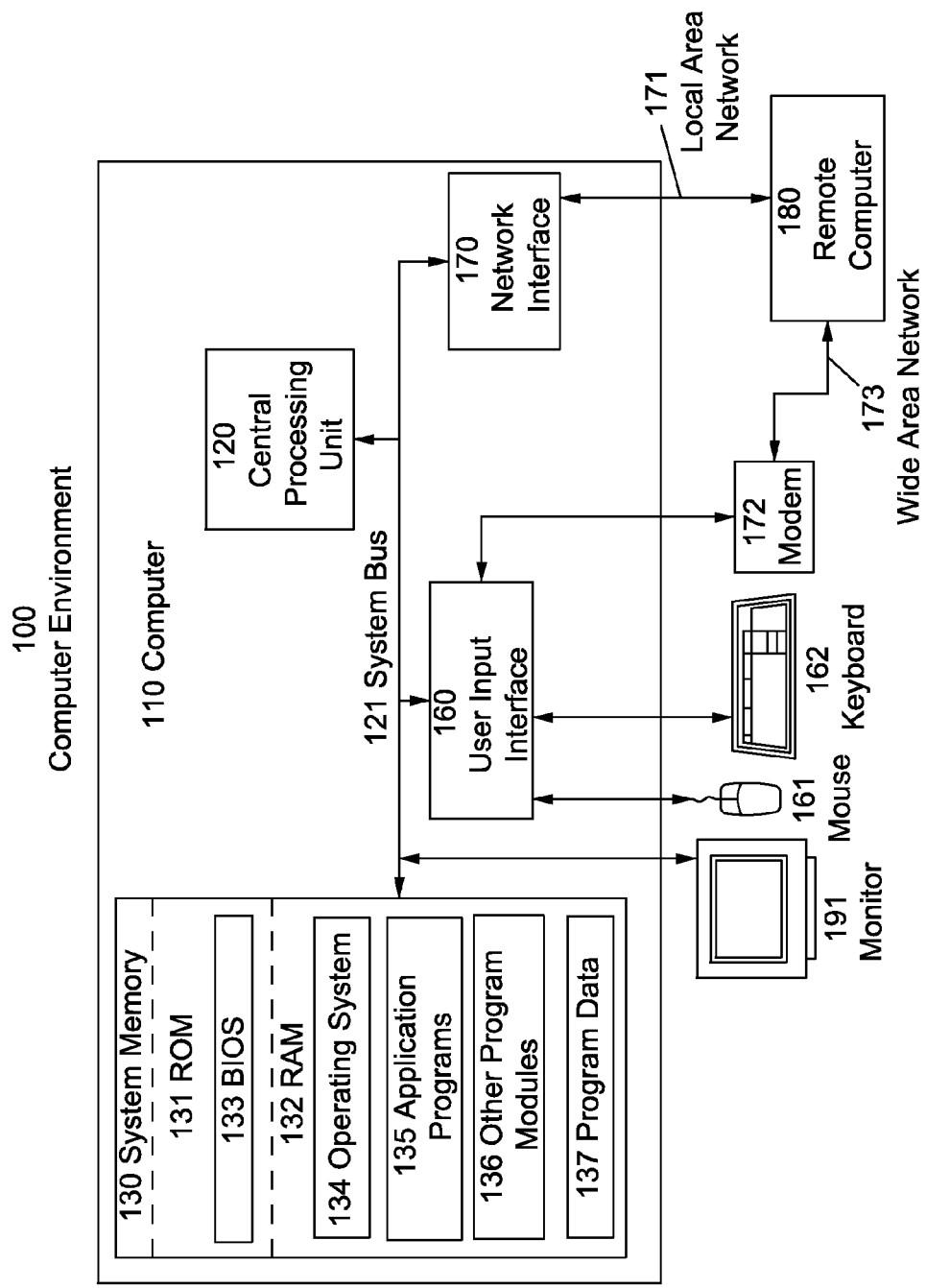
FIG. 23 is a block diagram of an example computing environment in which an example embodiment may be implemented.

FIG. 23 depicts an example computing environment 100 (e.g., the computer system or PC shown in FIGS. 1 and 21) in which an example embodiment may be implemented. Computing environment 100 may include computer 110, monitor 191 and other input or output devices such as mouse 161, keyboard 162 and modem 172. Computers and computing environments, such as computer 110 and computing environment 100, are known to those skilled in the art and thus are briefly described here.

An example system for implementing an embodiment includes a general purpose computing device in the form of computer 110. Components of computer 110 may include central processing unit 120, system memory 130 and system bus 121 that couples various system components including the system memory to processing unit 120.

System memory 130 may include computer storage media in the form of volatile and/or nonvolatile memory such as ROM 131 and RAM 132. A basic input/output system 133 (BIOS) containing the basic routines that help to transfer information between elements within computer 110, such as during start-up, may be stored in ROM 131. RAM 132 typically contains data and/or program modules that are immediately accessible to and/or presently being operated on by central processing unit 120. System memory 130 additionally may include, for example, operating system 134, application programs 135, other program modules 136 and program data 137.

Embodiments may be implemented in computing environment 100 in the form of any of a variety of computer readable media. Computer readable media can be any media that can be accessed by computer 110, including both volatile and nonvolatile, removable and non-removable media.

Computer 110 may operate in a networked environment using logical connections to one or more remote computers, such as remote computer 180. Remote computer 180 may be a personal computer, a server, a router, a network PC, a peer device or other common network node, and typically includes many or all of the elements described above relative to computer 110. The logical connections depicted in FIG. 1 include local area network (LAN) 171 and wide area network (WAN) 173, but may also include other networks. Such networking environments may be common in offices, enterprise-wide computer networks, intranets, and the Internet.

When used in a LAN networking environment, computer 110 may be connected to LAN 171 through network interface 170. When used in a WAN 173 networking environment, computer 110 may include modem 172 for establishing communications over WAN 173, such as the Internet. Modem 172 may be connected to system bus 121 via user input interface 160, or other appropriate mechanism.

Computer 110 or other client device can be deployed as part of a computer network. In this regard, various embodiments pertain to any computer system having any number of memory or storage units, and any number of applications and processes occurring across any number of storage units or volumes. An embodiment may apply to an environment with server computers and client computers deployed in a network environment, having remote or local storage. An embodiment may also apply to a standalone computing device, having programming language functionality, interpretation and execution capabilities.

Tooling Mounting Options

Figure 24:
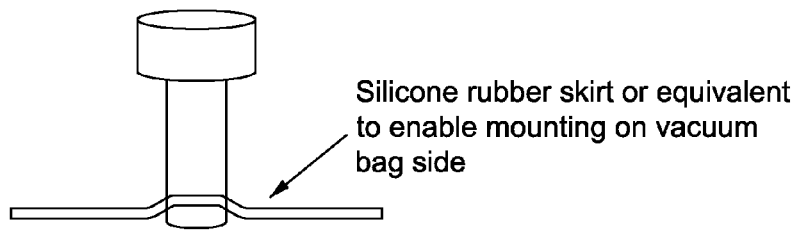
FIG. 24 shows exemplary tooling mounting options, including a silicone rubber skirt.
Figure 25:
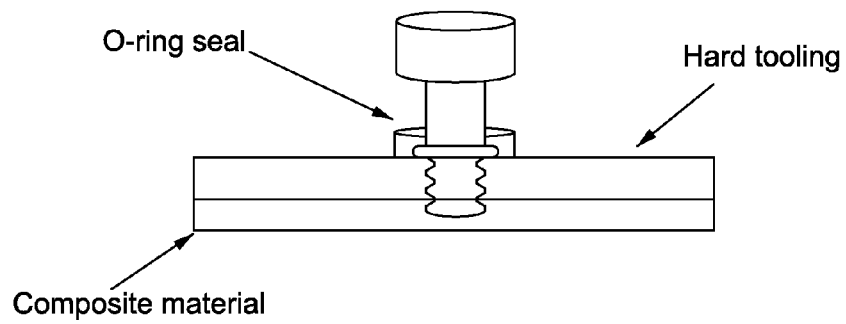
FIG. 25 shows exemplary tooling mounting options, including a hard mounting option.
Figure 26:
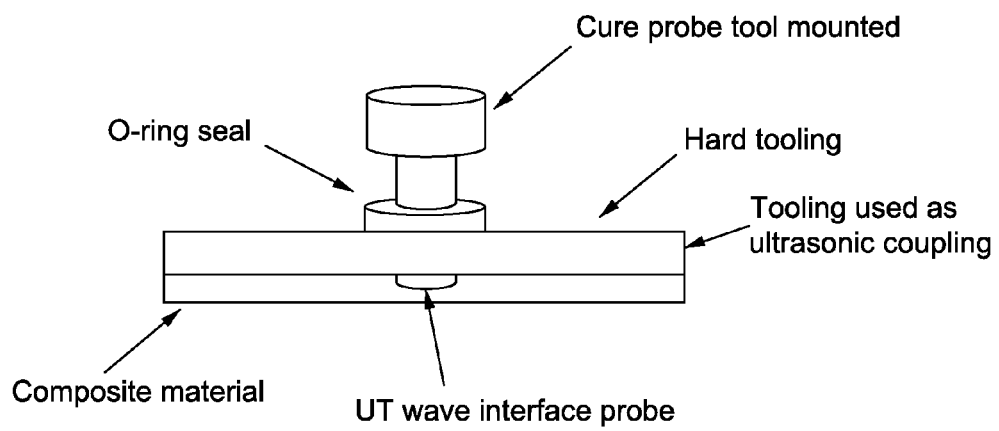
FIG. 26 shows exemplary tooling hard mounting options with solid tooling providing ultrasonic wave path to the interface probe.

In some embodiments, the waveguide can be made integral to the composite parts-tooling, or the waveguide probe can integrate tooling material or tooling surfaces as an extension to the ultrasonic path. FIGS. 24-26 show several embodiments having tooling mounting options. As shown in FIG. 24, a silicone rubber skirt or equivalent may be provided proximate the distal end of the probe to enable mounting of the probe on a vacuum bag side. As shown, the probe waveguide may extend through a hole or opening in the skirt and the tip or front face of the probe may contact the material being cured. In another embodiment, the tool mount may include hard tooling, such as shown in FIGS. 25 and 26. The hard tooling may be in contact with the materials being cured and may be used as a means of ultrasonic coupling of the waveguide probe to the composite material. As shown, a seal, for example an o-ring seal, may be provided between the probe waveguide extension and the tooling.

Critical Angle Reflection Probes

Figure 27:
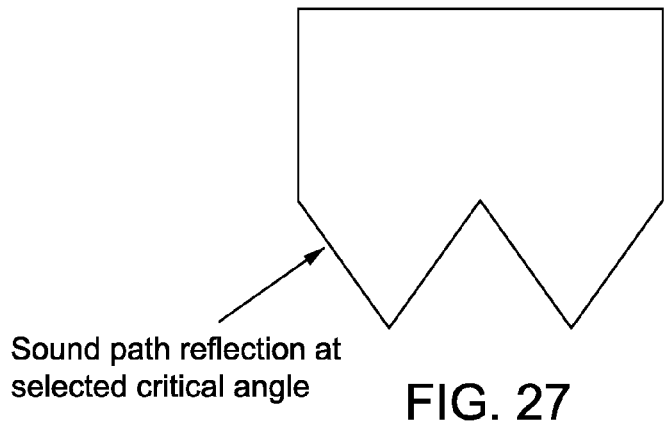
FIG. 27 shows an exemplary schematic design of a multi-element cure sensing interface critical angle reflection probe.
Figure 28:
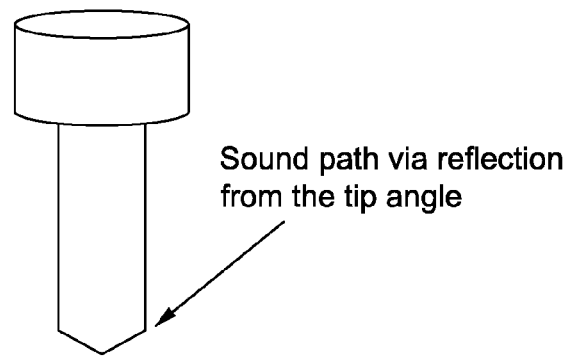
FIG. 28 shows an exemplary single element critical angle reflection probe.
Figure 29:
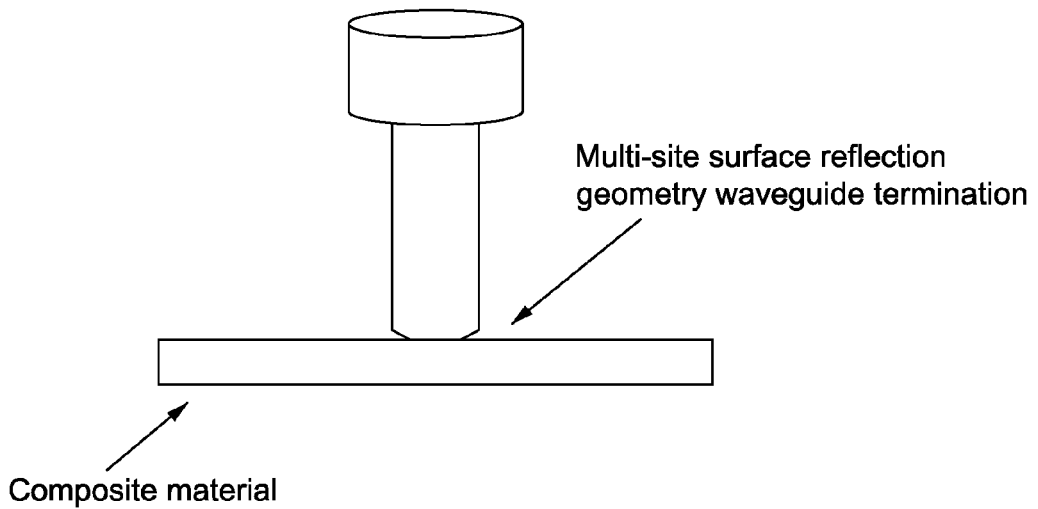
FIG. 29 shows another exemplary critical angle reflection probe having multi-site surface reflection geometry at the waveguide cure sensing interface termination.

FIGS. 27-29 show several probe embodiments having critical angle reflection geometries at the probe tip. As shown in FIG. 27, an exemplary critical angle reflection probe may include a tip geometry having multiple angled structures. The shape and angle of the probe tip may be selected based on the particular application and the desired critical angle. Also shown is the sound path reflection at the selected critical angle. FIG. 28 shows a probe having a single tip angle for producing the desired sound path via reflection for the tip angle. FIG. 29 shows a multi-surface reflection geometry waveguide termination in contact with a composite material.

DEFINITIONS

Curing is a term in polymer chemistry and process engineering that refers to the toughening or hardening of a polymer material by cross-linking of polymer chains, typically brought about by chemical additives, ultraviolet radiation, electron beam or heat. The curing process transforms the resin into a plastic or rubber by a cross-linking process. Despite the wide variety of thermo-set resin formulations (epoxy, vinylester, polyester, etc.), their cure behavior is qualitatively identical. The resin viscosity drops initially upon the application of heat, passes through a region of maximum flow and begins to increase as the chemical reactions increase the average length and the degree of cross-linking between the constituent oligomers. This process continues until a continuous 3-dimensional structure is created. Cure monitoring methods give a significant insight to the chemical process and define process actions towards achieving specific quality indices of the cured resin systems.

Real-time computing of cure monitoring is an essential component for the control of the manufacturing process of composite materials. The rationale for cure monitoring relies on the various physical and/or chemical properties that can be used to follow the transformation of an initially liquid thermo-set resin into its final rigid solid form (curing).

Cure material includes thermosetting plastics (thermosets) and polymer materials that irreversibly cure. Examples of materials that may be cure include, but are not limited to: polymers; polymer composites; polyester fiberglass systems; fiber reinforced composite materials; vulcanized rubber; resins; polymeric resins; phenol-formaldehyde resin; urea-formaldehyde foam; melamine resin; epoxy resin; polyamides; and the like.

A waveguide is a device or structure designed to confine and direct the propagation of waves (i.e., that guides waves), such as sound or light waves. An acoustical waveguide is a physical structure for guiding sound waves.

An ultrasonic transducer is a device that generates and sends high frequency sound waves. An ultrasonic transducer may also receive back the echo of the high frequency sound waves. An example of an ultrasonic transducer is a piezoelectric transducer that converts electrical energy into sound waves. Upon receipt of the echo, the ultrasonic transducer turns the sound wave into electrical energy which can be measured. An ultrasonic transducer may generate sound waves above about 20,000 Hz. The transmitter and receiver components may comprise separate devices or may be combined in a single device. One use for ultrasonic transducers is non-destructive testing.

Non-cure related signal variances are effects caused by one or more of: temperature effects, pressure effects, humidity effects, variances in transducer response, variances in waveguide response, variances in overall probe response, variances in instrument and signal channel response, and the like. Non-cure related signal variances may be compensated for or corrected using the differential ultrasonic waveguide cure monitoring probe and the independent calibrated response manner.

The differential ultrasonic waveguide cure monitoring probe has been demonstrated to be very sensitive to different stages of a cure cycle and appears to be effective in quantitative determination of the final cure. The benefits of this configuration are based on the simplicity of the probe, low cost of the wave-guide, ability to quantitatively calibrate the signals and ability to configure the probe to a variety of resins and processes. The ultrasonic waves are very sensitive to the interface impedance changes and the differential ultrasonic waveguide cure monitoring probe (UCS) is adapted to utilize and maximize this phenomenon.

Overall, the UCS probe approach with $R_{RRC}$ signal sensing has many application advantages/benefits including:

The probe design is very inexpensive.

All transducers, cables and instrumentation are reusable.

The sensor system can be calibrated and is suitable for final cure tracking.

Ultrasonic resin cure determination is a more direct measure of the mechanical state of a resin than other types of cure sensors.

The sensor design is adaptable to modern ultrasonic instrumentation that can multiplex signals and support many channels.

Sensor fundamental design has robustness and is adaptable for wide range of resin types by modifications and customization of the probe ρc properties.

The probe design enables absolute calibration on ultrasonic signal amplitude.

The probe design further enables the measurement of the differential temperature effects allowing for the correction of the signal amplitude changes due to temperature.

Integrating probe response with signal capture and processing functions enables quantitative multi-sensor cure response comparison.

While the present invention has been described in connection with the exemplary embodiments of the various Figures, it is not limited thereto and it is to be understood that other similar embodiments may be used or modifications and additions may be made to the described embodiments for performing the same function of the present invention without deviating therefrom. Therefore, the present invention should not be limited to any single embodiment, but rather should be construed in breadth and scope in accordance with the appended claims. Also, the appended claims should be construed to include other variants and embodiments of the invention, which may be made by those skilled in the art without departing from the true spirit and scope of the present invention.

What is claimed:

1. A differential ultrasonic waveguide cure monitoring probe for in situ ultrasonic monitoring of a material undergoing a cure process, the probe comprising:
   an ultrasonic transducer;
   a waveguide having a proximal end in contact with the ultrasonic transducer and a distal end for contacting the material undergoing the cure process, the waveguide comprising:
     a first portion extending from the proximal end;
     a reference of the waveguide;
     a second portion extending from the reference to a tip at the distal end of the waveguide;
   wherein the tip further comprises a lip located on the circumference of the tip;
   wherein an ultrasonic signal can be generated by the ultrasonic transducer and transmitted into the waveguide;
   thereby generating an interface signal by a portion of the ultrasonic signal reflecting back from the interface of the probe and the material undergoing a cure, the interface signal reflecting back to the ultrasonic transducer, the interface signal being used to directly sense the mechanical modulus change of the curing material; and
   thereby generating a reference signal by a portion of the ultrasonic signal reflecting back from the reference, the reference signal reflecting back to the ultrasonic transducer, the reference signal being used to recalibrate the probe and account for non-cure related signal variances during the cure process;
   wherein a quantitative assessment of a cure level of the material undergoing the cure process is determined in a non-cure related signal variances independent calibrated response manner using the reference signal to correct/recalibrate the interface signal.

2. The differential ultrasonic waveguide cure monitoring probe of claim 1, wherein the response signal is internal to the probe and independently influenced by the probe environment and can be used to continuously correct and recalibrate the probe response as measured by the interface signal, which measures changes in signal reflection/transmission due to impedance change in the curing material.

3. The differential ultrasonic waveguide cure monitoring probe of claim 1, wherein the waveguide reference further comprises a cross-section reference, the cross-sectional reference comprising:
   a first portion having an first cross-sectional area; and
   a second portion having a second cross-sectional area, the second cross-sectional area being smaller that the first cross-sectional area;
   wherein the reference is the portion of the first cross-sectional area that extends beyond the second cross-sectional area.

4. The differential ultrasonic waveguide cure monitoring probe of claim 1, wherein the waveguide reference further comprises a slot reference, the slot reference comprising a slot in the waveguide extending from a side of the waveguide toward a center of the waveguide and substantially orthogonal to a longitudinal centerline of the waveguide.

5. The differential ultrasonic waveguide cure monitoring probe of claim 1, wherein the waveguide reference further comprises a small transducer cross-section reference.

6. The differential ultrasonic waveguide cure monitoring probe of claim 1, wherein the waveguide reference further comprises an insert/void reference.

7. The differential ultrasonic waveguide cure monitoring probe of claim 1, wherein the waveguide further comprises an alternate geometry, the alternate geometry comprising an angled body wherein the second portion of the waveguide extends at an angle relative to the first portion of the waveguide.

8. The differential ultrasonic waveguide cure monitoring probe of claim 1, wherein the probe is in direct contact with the material undergoing the cure process, the probe is only connected to one side of the material being cured, and the cure monitoring is performed in situ to allow real time monitoring of the cure process.

9. The differential ultrasonic waveguide cure monitoring probe of claim 1, wherein the probe is initially calibrated before the cure process using a material having known characteristics and wherein the probe is continuously calibrated during the cure process using the reference signal to account for non-cure related signal variances during the cure process in order to provide quantitative assessment and comparison of cure rates and degree of cure completion.

10. The differential ultrasonic waveguide cure monitoring probe of claim 1, wherein the material being cured comprises any thermo-setting material.

11. The differential ultrasonic waveguide cure monitoring probe of claim 1, further comprising a front face located at the tip, the front surface suitable for direct contact with the cure material and for ensuring coupling of the ultrasonic signal across the probe/material interface.

12. The differential ultrasonic waveguide cure monitoring probe of claim 11, wherein the tip and front face further comprise a critical angle reflection structure.

13. The differential ultrasonic waveguide cure monitoring probe of claim 12, wherein the critical angle reflection structure further comprises multiple surface refection geometry waveguide terminations.

14. A differential ultrasonic waveguide cure monitoring probe for in situ ultrasonic monitoring of a material undergoing a cure process, the probe comprising:
an ultrasonic transducer;
a waveguide having a proximal end in contact with the ultrasonic transducer and a distal end for contacting the material undergoing the cure process, the waveguide comprising:
a first portion extending from the proximal end;
a reference of the waveguide;
a second portion extending from the reference to a tip at the distal end of the waveguide;
wherein the waveguide further comprises an alternate geometry, the alternate geometry comprising an angled body wherein the second portion of the waveguide extends at an angle relative to the first portion of the waveguide;
wherein an ultrasonic signal can be generated by the ultrasonic transducer and transmitted into the waveguide;
thereby generating an interface signal by a portion of the ultrasonic signal reflecting back from the interface of the probe and the material undergoing a cure, the interface signal reflecting back to the ultrasonic transducer, the interface signal being used to directly sense the mechanical modulus change of the curing material; and
thereby generating a reference signal by a portion of the ultrasonic signal reflecting back from the reference, the reference signal reflecting back to the ultrasonic transducer, the reference signal being used to recalibrate the probe and account for non-cure related signal variances during the cure process;
wherein a quantitative assessment of a cure level of the material undergoing the cure process is determined in a non-cure related signal variances independent calibrated response manner using the reference signal to correct/recalibrate the interface signal.

15. A differential ultrasonic waveguide cure monitoring system comprising:
a differential ultrasonic waveguide cure monitoring probe according to claim 1 or claim 14;
a computer coupled to the differential ultrasonic waveguide cure monitoring probe, the computer comprising:
an input device for receiving information relating to the reference signal and the interface signal;
a processor for analyzing the information relating to the reference signal and the interface signal and for distinguishing the propagation differences between the response signal and the interface signal to estimate the cure material modulus to determine a quantitative cure state of the material in a non-cure related signal variances independent calibrated response manner;
a data storage device for storing one or more of: the information relating to the reference signal and the interface signal, information relating to the material being cured, and information relating to the cure process;
an output device for outputting one or more of: the information relating to the reference signal and the interface signal, information relating to the material being cured, and information relating to the cure process.

16. The system of claim 15, further comprising:
a signal gate for controlling sampling rate;
an A/D converter;
a pulser/receiver card for controlling pulse generation and receipt of the reflected signals; and
a channel multiplexer board for signal multiplexing.

17. The system of claim 15, wherein the probe is integrated into new computerized cure process monitoring system.

18. The system of claim 15, wherein the probe is retrofit into existing materials processing assemblies.

19. The system of claim 15, further comprising tooling mounting options for coupling the differential ultrasonic waveguide probe to the material to be cured.

* * * * *